(12) United States Patent
Geiselhart et al.

(10) Patent No.: US 7,455,063 B2
(45) Date of Patent: Nov. 25, 2008

(54) ADJUSTABLE GAS DELIVERY MASK HAVING A FLEXIBLE GASKET

(75) Inventors: Ed Geiselhart, Chicago, IL (US); Chris Houghton, Chicago, IL (US); Erik Holverson, Naperville, IL (US); Brian Woodard, Chicago, IL (US); Benjamin K. Sun, San Francisco, CA (US)

(73) Assignee: Nellcor Puritan Bennett LLC, North Haven, CT (US)

( * ) Notice: Subject to any disclaimer, the term of this patent is extended or adjusted under 35 U.S.C. 154(b) by 521 days.

(21) Appl. No.: 11/156,047

(22) Filed: Jun. 17, 2005

(65) Prior Publication Data

US 2006/0283459 A1 Dec. 21, 2006

(51) Int. Cl.
*A61M 11/00* (2006.01)

(52) U.S. Cl. .............. 128/205.25; 128/207.13; 128/206.24; 128/206.27

(58) Field of Classification Search ............. 128/205.25, 128/207.13, 206.26, 206.24, 206.27
See application file for complete search history.

(56) References Cited

U.S. PATENT DOCUMENTS

| | | | | |
|---|---|---|---|---|
| 1,081,745 | A * | 12/1913 | Johnston et al. ........ | 128/203.25 |
| 1,532,195 | A | 4/1925 | Morrison | |
| 1,911,938 | A | 5/1933 | Bard | |
| 2,130,155 | A | 9/1938 | Malcom | |
| 2,428,451 | A | 10/1947 | Emerson | |
| 4,069,516 | A | 1/1978 | Watkins, Jr. ............ | 72/201 |
| 4,275,908 | A | 6/1981 | Elkins et al. ........... | 285/55 |
| 4,373,520 | A | 2/1983 | Arbique ................. | 128/201.19 |
| 4,498,472 | A | 2/1985 | Tanaka .................. | 128/205.17 |
| 4,539,983 | A | 9/1985 | Angell .................. | 128/201.19 |
| 4,739,755 | A | 4/1988 | White et al. ........... | 128/206.12 |
| 4,799,263 | A | 1/1989 | Banziger et al. ........ | 381/94 |

(Continued)

FOREIGN PATENT DOCUMENTS

EP 1025875 2/2000

(Continued)

OTHER PUBLICATIONS

International Search Report with Written Opinion, PCT/US2006/023083, 12 pages, Oct. 4, 2006.

(Continued)

*Primary Examiner*—Steven O Douglas
(74) *Attorney, Agent, or Firm*—Baker Botts L.L.P.

(57) ABSTRACT

In accordance with one embodiment of the present disclosure, an adjustable gas delivery system is provided. The system may include a face mask, an arm apparatus, and a gasket. The face mask may be configured to deliver gas to a subject, and may include a flexible cushion portion configured to interface with the subject's face and a rigid base portion configured to support the cushion portion, the rigid base portion including a gas inlet. The arm apparatus may be configured to deliver gas to the face mask. The arm apparatus may include a gas outlet having a cross-sectional area smaller than a cross-sectional area of the gas inlet of the base portion of the face mask. The gasket may couple the gas outlet of the arm apparatus with the gas inlet of the face mask. The gasket may be flexible such that the orientation of the face mask relative to the arm apparatus is adjustable.

21 Claims, 22 Drawing Sheets

U.S. PATENT DOCUMENTS

| | | | |
|---|---|---|---|
| 4,843,686 A | 7/1989 | Bartholomew | 24/19 |
| 4,886,056 A | 12/1989 | Simpson | 128/201.25 |
| 4,915,106 A | 4/1990 | Aulgur et al. | 128/207.11 |
| 4,938,209 A | 7/1990 | Fry | 128/200.21 |
| 4,958,633 A | 9/1990 | Angell | 128/201.19 |
| 4,960,121 A | 10/1990 | Nelson et al. | 128/206.24 |
| 4,989,596 A | 2/1991 | Macris et al. | 128/201.28 |
| 5,036,846 A | 8/1991 | Aulgur et al. | 128/207.11 |
| 5,038,776 A | 8/1991 | Harrison et al. | 128/207.11 |
| 5,058,244 A | 10/1991 | Fernandez | 24/170 |
| D321,418 S | 11/1991 | Dolida et al. | D29/7 |
| 5,069,205 A | 12/1991 | Urso | 128/201.24 |
| 5,074,297 A | 12/1991 | Venegas | 124/204.18 |
| 5,181,280 A | 1/1993 | Zachry, Jr. | 2/452 |
| 5,181,507 A | 1/1993 | Michel et al. | 128/201.25 |
| 5,199,424 A | 4/1993 | Sullivan et al. | 128/204.18 |
| 5,269,296 A | 12/1993 | Landis | 128/207.18 |
| 5,353,789 A | 10/1994 | Schlobohm | 128/206.24 |
| 5,429,126 A | 7/1995 | Bracken | 128/207.11 |
| 5,441,046 A | 8/1995 | Starr et al. | 128/207.11 |
| 5,463,693 A | 10/1995 | Birli et al. | 381/75 |
| 5,503,147 A | 4/1996 | Bertheau | 128/207.11 |
| 5,517,986 A | 5/1996 | Starr et al. | 128/206.24 |
| 5,537,994 A | 7/1996 | Thornton | 128/204.18 |
| 5,623,923 A | 4/1997 | Bertheau et al. | 128/207.11 |
| 5,628,305 A | 5/1997 | Melker | 128/202.29 |
| 5,662,101 A | 9/1997 | Ogden et al. | 128/205.25 |
| 5,697,363 A | 12/1997 | Hart | 128/201.24 |
| 5,724,965 A | 3/1998 | Handke et al. | 128/207.13 |
| 5,921,239 A | 7/1999 | McCall et al. | 128/205.25 |
| 5,941,245 A | 8/1999 | Hannah et al. | 128/207.11 |
| 6,039,045 A | 3/2000 | Bertheau et al. | 128/207.11 |
| 6,041,781 A | 3/2000 | Aglan | 128/205.17 |
| 6,044,844 A | 4/2000 | Kwok et al. | 128/207.11 |
| 6,112,746 A | 9/2000 | Kwok et al. | 128/207.13 |
| 6,119,694 A | 9/2000 | Correa et al. | 128/207.13 |
| 6,123,071 A | 9/2000 | Berthon-Jones et al. | 128/204.18 |
| 6,155,253 A | 12/2000 | Gamberini | 128/201.18 |
| 6,182,298 B1 | 2/2001 | Dampney | 2/422 |
| 6,192,886 B1 | 2/2001 | Rudolph | 128/207.13 |
| 6,263,874 B1 | 7/2001 | LeDez et al. | 128/206.21 |
| 6,279,172 B1 | 8/2001 | Epperson et al. | 2/410 |
| 6,338,342 B1 | 1/2002 | Fecteau et al. | 128/207.11 |
| 6,347,631 B1 | 2/2002 | Hansen et al. | 128/207.11 |
| 6,357,441 B1 | 3/2002 | Kwok et al. | 128/207.13 |
| 6,374,824 B1 | 4/2002 | Thornton | 128/201.26 |
| 6,374,826 B1 | 4/2002 | Gunaratnam et al. | 128/206.27 |
| 6,382,206 B1 | 5/2002 | Palazzotto et al. | 128/201.19 |
| 6,386,198 B1 | 5/2002 | Rugless | 128/206.21 |
| 6,435,181 B1 | 8/2002 | Jones, Jr. et al. | 128/204.18 |
| 6,439,230 B1 | 8/2002 | Gunaratnam et al. | 128/206.21 |
| 6,463,931 B1 | 10/2002 | Kwok et al. | 128/207.11 |
| 6,467,483 B1 | 10/2002 | Kopacko et al. | 128/207.12 |
| 6,470,886 B1 | 10/2002 | Jestrabek-Hart | 128/207.11 |
| 6,494,207 B1 | 12/2002 | Kwok | 128/207.11 |
| 6,497,232 B2 | 12/2002 | Fecteau et al. | 128/207.11 |
| 6,505,623 B1 | 1/2003 | Hansen | 128/207.11 |
| 6,516,802 B2 | 2/2003 | Hansen et al. | 128/207.11 |
| 6,530,373 B1 | 3/2003 | Patron et al. | 128/205.25 |
| 6,532,961 B1 | 3/2003 | Kwok et al. | 128/206.21 |
| 6,536,435 B1 | 3/2003 | Fecteau et al. | 128/206.21 |
| 6,539,941 B2 | 4/2003 | Haubeil | 128/205.13 |
| 6,543,445 B1 | 4/2003 | Hopper | 128/200.4 |
| 6,571,797 B1 | 6/2003 | Magidson et al. | 128/205.27 |
| 6,581,602 B2 | 6/2003 | Kwok et al. | 128/207.13 |
| 6,591,837 B1 | 7/2003 | Byram | 128/206.24 |
| 6,615,830 B1 | 9/2003 | Serowski et al. | 128/202.27 |
| 6,615,834 B2 | 9/2003 | Gradon et al. | 128/207.11 |
| 6,619,288 B2 | 9/2003 | Demers et al. | 128/205.25 |
| 6,626,178 B2 | 9/2003 | Morgan et al. | 128/206.26 |
| 6,629,532 B2 | 10/2003 | Campbell, Sr. | 128/207.11 |
| D486,226 S | 2/2004 | Guney et al. | D24/110.1 |
| D486,907 S | 2/2004 | Guney et al. | D24/110.1 |
| 6,691,708 B2 | 2/2004 | Kwok et al. | 128/207.11 |
| 6,694,973 B1 | 2/2004 | Dunhao et al. | 128/203.12 |
| 6,701,926 B2 | 3/2004 | Olsen et al. | 128/207.11 |
| 6,701,927 B2 | 3/2004 | Kwok et al. | 128/207.13 |
| 6,729,333 B2 | 5/2004 | Barnett et al. | 128/207.13 |
| 6,732,733 B1 | 5/2004 | Brostrom et al. | 128/206.27 |
| 6,745,770 B2 | 6/2004 | McAuliffe et al. | 128/205.24 |
| 6,745,772 B1 | 6/2004 | McLeod | 128/206.21 |
| 6,772,760 B2 | 8/2004 | Frater et al. | 128/206.24 |
| 6,776,161 B2 | 8/2004 | Horn | 128/207.11 |
| 6,789,541 B2 | 9/2004 | Olsen et al. | 128/207.11 |
| 6,792,947 B1 | 9/2004 | Bowden | 128/205.17 |
| 6,805,117 B1 | 10/2004 | Ho et al. | 128/201.22 |
| 6,820,615 B1 | 11/2004 | Feng | 128/201.27 |
| 6,851,428 B2 | 2/2005 | Dennis | 128/205.25 |
| 6,854,465 B2 | 2/2005 | Bordewick et al. | 128/207.11 |
| 6,883,519 B2 | 4/2005 | Schmidtke et al. | 128/207.11 |
| 6,886,564 B2 | 5/2005 | Sullivan et al. | 128/206.24 |
| 6,895,964 B2 | 5/2005 | McAuliffe et al. | 128/205.24 |
| 6,907,882 B2 | 6/2005 | Ging et al. | 128/207.11 |
| 6,926,004 B2 | 8/2005 | Schumacher | 128/206.27 |
| 6,926,007 B2 | 8/2005 | Frank | 128/846 |
| 6,951,218 B2 | 10/2005 | Gradon et al. | 128/205.25 |
| 6,959,710 B2 | 11/2005 | Barnett et al. | 128/207.13 |
| 6,981,503 B1 | 1/2006 | Shapiro | 128/845 |
| 7,017,576 B2 | 3/2006 | Olsen et al. | 128/205.25 |
| 7,017,579 B2 | 3/2006 | Palmer | 128/207.17 |
| 7,036,508 B2 | 5/2006 | Kwok | 128/207.11 |
| 7,047,971 B2 | 5/2006 | Ho et al. | 128/207.11 |
| 7,047,972 B2 | 5/2006 | Ging et al. | 128/207.11 |
| 7,066,179 B2 | 6/2006 | Eaton et al. | 128/206.27 |
| 7,089,941 B2 | 8/2006 | Bordewick et al. | 128/207.11 |
| 7,096,867 B2 | 8/2006 | Smith et al. | 128/207.11 |
| 7,188,620 B2 | 3/2007 | Amarasinghe | 128/201.22 |
| 7,201,169 B2 | 4/2007 | Wilkie et al. | 128/207.18 |
| 7,231,921 B2 | 6/2007 | Palmer | 128/207.17 |
| 7,318,439 B2 | 1/2008 | Raje et al. | 128/206.24 |
| 7,320,323 B2 | 1/2008 | Lang et al. | 128/206.24 |
| 2002/0096176 A1 | 7/2002 | Gunaratnam et al. | 128/207.11 |
| 2002/0148473 A1 | 10/2002 | Kwok et al. | 128/207.11 |
| 2002/0157668 A1 | 10/2002 | Bardel | 128/201.22 |
| 2002/0189616 A1 | 12/2002 | Wolf | 128/205.25 |
| 2003/0000001 A1 | 1/2003 | McDonald et al. | 2/6.3 |
| 2003/0005935 A1 | 1/2003 | Kwok et al. | 128/206.21 |
| 2003/0019496 A1 | 1/2003 | Kopacko et al. | 128/206.24 |
| 2003/0051732 A1 | 3/2003 | Smith et al. | 128/206.27 |
| 2003/0075180 A1 | 4/2003 | Raje et al. | 128/206.24 |
| 2003/0075182 A1 | 4/2003 | Heidmann et al. | 128/207.11 |
| 2003/0084903 A1 | 5/2003 | Fecteau et al. | 128/206.27 |
| 2003/0087033 A1 | 5/2003 | Ramsay | 427/282 |
| 2003/0127096 A1 | 7/2003 | McAuliffe et al. | 128/204.18 |
| 2003/0127101 A1 | 7/2003 | Dennis | 128/206.21 |
| 2003/0196655 A1 | 10/2003 | Ging et al. | 128/201.22 |
| 2003/0217746 A1 | 11/2003 | Gradon et al. | 128/201.26 |
| 2003/0221691 A1 | 12/2003 | Biener et al. | 128/206.24 |
| 2004/0025882 A1 | 2/2004 | Madaus et al. | 128/206.27 |
| 2004/0034519 A1 | 2/2004 | Huitouze et al. | 704/1 |
| 2004/0065328 A1 | 4/2004 | Amarasinghe et al. | 128/206.27 |
| 2004/0073989 A1 | 4/2004 | Horn | 2/42 |
| 2004/0083534 A1 | 5/2004 | Ruiz et al. | 2/171.2 |
| 2004/0107964 A1 | 6/2004 | Shaw | 128/203.22 |
| 2004/0112377 A1 | 6/2004 | Amarasinghe et al. | 128/201.22 |
| 2004/0112384 A1 | 6/2004 | Lithgow et al. | 128/206.21 |
| 2004/0118406 A1 | 6/2004 | Lithgow et al. | 128/206.24 |
| 2004/0182396 A1 | 9/2004 | Dennis | 128/205.25 |
| 2004/0182398 A1 | 9/2004 | Sprinkle et al. | 128/207.13 |
| 2004/0194783 A1 | 10/2004 | McAuliffe et al. | 128/205.24 |
| 2004/0216746 A1 | 11/2004 | Jones, Jr. et al. | 128/206.21 |
| 2004/0221850 A1 | 11/2004 | Ging et al. | 128/206.27 |

| | | | | | |
|---|---|---|---|---|---|
| 2004/0226566 A1 | 11/2004 | Gunaratnam et al. ... 128/207.18 | EP | 1356843 | 4/2003 |
| 2004/0255949 A1 | 12/2004 | Lang et al. ............. 128/206.21 | EP | 1334742 | 8/2003 |
| 2005/0051171 A1 | 3/2005 | Booth .................... 128/206.18 | EP | 1334742 A2 | 8/2003 |
| 2005/0072428 A1 | 4/2005 | Ho et al. ................ 128/205.25 | FR | 1083873 | 1/1955 ..................... 5/3 |
| 2005/0076913 A1 | 4/2005 | Ho et al. ................ 128/206.27 | JP | 2000102615 | 4/2000 |
| 2005/0081858 A1 | 4/2005 | Raje et al. .............. 128/206.21 | JP | 2003175106 | 6/2003 |
| 2005/0155604 A1 | 7/2005 | Ging et al. ............. 128/206.21 | WO | 00/50122 | 8/2000 |
| 2005/0205096 A1 | 9/2005 | Matula, Jr. et al. ..... 128/207.11 | WO | 0100266 A2 | 1/2001 |
| 2005/0279367 A1 | 12/2005 | Klemperer .................. 128/861 | WO | 02/15968 | 2/2002 |
| 2005/0284481 A1 | 12/2005 | Meyer et al. ........... 128/207.11 | WO | 02096342 A2 | 12/2002 |
| 2006/0000476 A1 | 1/2006 | Salem ................... 128/206.21 | WO | 03/008044 | 1/2003 |
| 2006/0027236 A1 | 2/2006 | Barnett et al. .......... 128/206.24 | WO | 03/033077 | 4/2003 |
| 2006/0032504 A1 | 2/2006 | Burton et al. ........... 128/207.11 | WO | 03028613 A2 | 4/2003 |
| 2006/0042629 A1 | 3/2006 | Geist .................... 128/206.24 | WO | 2004/018014 | 3/2004 |
| 2006/0060200 A1 | 3/2006 | Ho et al. ................ 128/206.24 | WO | 2004/021960 | 3/2004 |
| 2006/0076019 A1 | 4/2006 | Ho ........................ 128/206.24 | WO | 2004/022146 | 3/2004 |
| 2006/0090760 A1 | 5/2006 | Gradon et al. .......... 128/206.27 | WO | 2004/022147 | 3/2004 |
| 2006/0112961 A1 | 6/2006 | Aly ....................... 128/206.11 | WO | 2004/041342 | 5/2004 |
| 2006/0118117 A1 | 6/2006 | Berthon-Jones et al. .................... 128/206.21 | WO | 2004/078228 | 9/2004 |
| 2006/0118119 A1 | 6/2006 | Berthon-Jones et al. .................... 128/207.11 | WO | 2004096332 A1 | 11/2004 |
| | | | WO | 2005021075 A1 | 3/2005 |
| | | | WO | 2005/034829 | 4/2005 |
| 2006/0162729 A1 | 7/2006 | Ging et al. ............. 128/206.27 | WO | 2005032634 A1 | 4/2005 |
| 2006/0174892 A1 | 8/2006 | Leksutin et al. ........ 128/207.11 | WO | 2005039680 A1 | 5/2005 |
| 2006/0191539 A1 | 8/2006 | Ho et al. ................ 128/207.11 | | | |
| 2006/0207600 A1 | 9/2006 | Burrow et al. ......... 128/207.11 | | | |
| 2006/0213521 A1 | 9/2006 | Radney ................. 128/207.11 | | | |
| 2006/0225740 A1 | 10/2006 | Eaton et al. ............ 128/206.24 | | | |
| 2006/0231102 A1 | 10/2006 | Bordewick et al. ..... 128/207.11 | | | |
| 2006/0231103 A1 | 10/2006 | Matula, Jr. et al. ..... 128/207.13 | | | |
| 2006/0272646 A1 | 12/2006 | Ho et al. ................ 128/207.11 | | | |
| 2006/0283456 A1 | 12/2006 | Geiselhart et al. ...... 128/206.24 | | | |
| 2006/0283458 A1 | 12/2006 | Woodard et al. ....... 128/206.24 | | | |
| 2006/0283460 A1 | 12/2006 | Brown et al. .......... 128/206.24 | | | |
| 2006/0283461 A1 | 12/2006 | Lubke et al. ........... 128/207.11 | | | |
| 2007/0017525 A1 | 1/2007 | Madaus et al. ......... 128/207.11 | | | |
| 2007/0028919 A1 | 2/2007 | Ho ........................ 128/204.18 | | | |
| 2007/0044797 A1 | 3/2007 | Ho ........................ 128/204.18 | | | |
| 2007/0062539 A1 | 3/2007 | Gunaratnam et al. ... 128/207.18 | | | |
| 2007/0107723 A1 | 5/2007 | Berg ..................... 128/200.26 | | | |

FOREIGN PATENT DOCUMENTS

| | | |
|---|---|---|
| EP | 0988869 | 3/2000 |
| EP | 1057494 B1 | 6/2000 |
| EP | 1057494 A2 | 12/2000 |
| EP | 1327458 | 1/2003 |

OTHER PUBLICATIONS

International Search Report with Written Opinion, PCT/US2006/023109, 13 pages, Oct. 6, 2006.
International Search Report with Written Opinion, PCT/US2006/023110, 4 pages, Oct. 9, 2006.
International Search Report with Written Opinion, PCT/US2006/023234, 11 pages, Oct. 13, 2006.
International Search Report with Written Opinion, PCT/US2006/023100, 10 pages, Oct. 17, 2006.
International Search Report with Written Opinion, PCT/US2006/023090, 19 pages, Oct. 30, 2006.
International Preliminary Report on Patentability PCT/US2006/023234, 7 pages, Jan. 3, 2008.
International Preliminary Report on Patentability PCT/US2006/023100, 6 pages, Jan. 3, 2008.
International Preliminary Report on Patentability PCT/US2006/023083, 7 pages, Jan. 3, 2008.
International Preliminary Report on Patentability PCT/US2006/023090, 10 pages., Jan. 3, 2008.

* cited by examiner

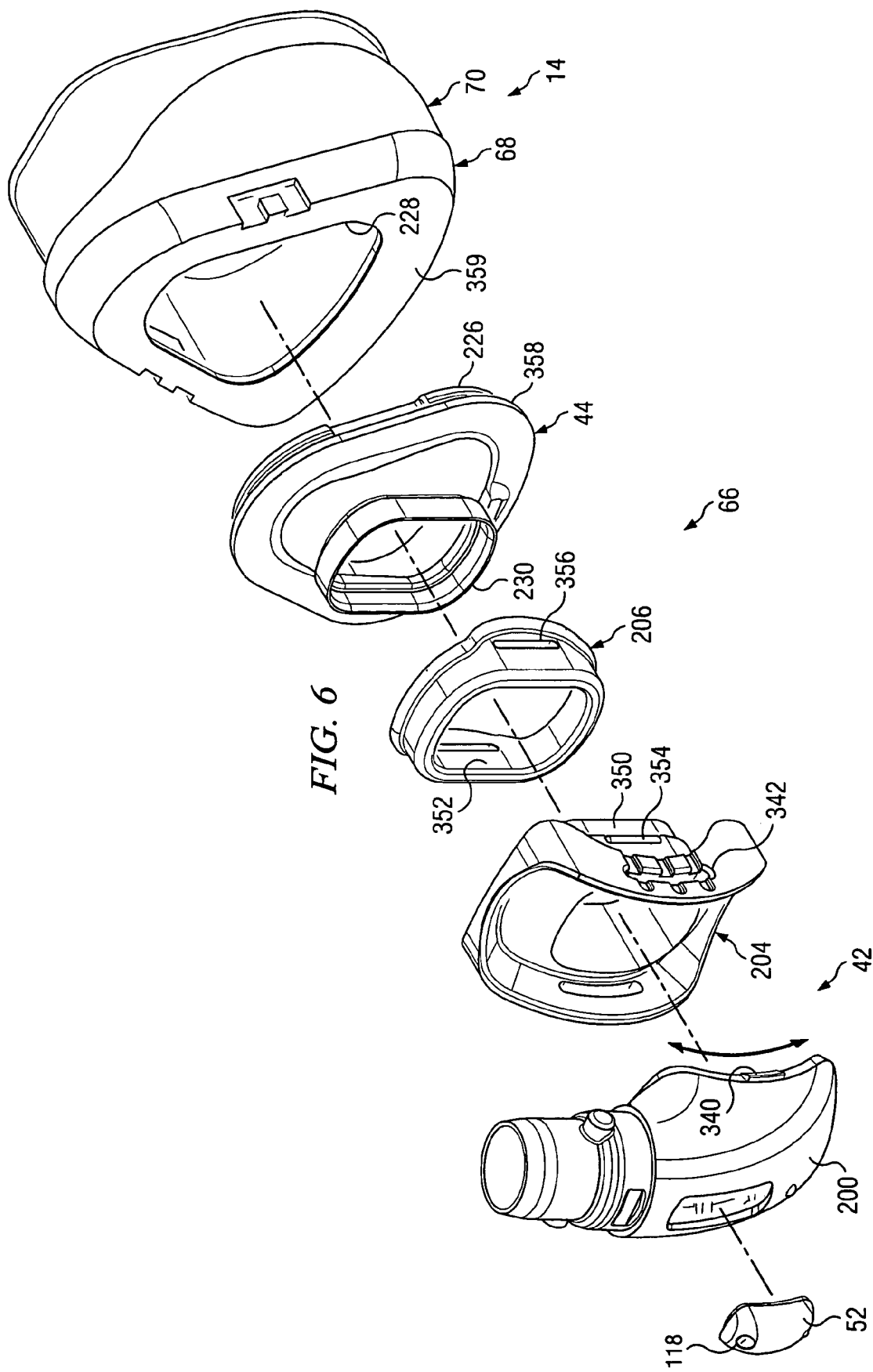

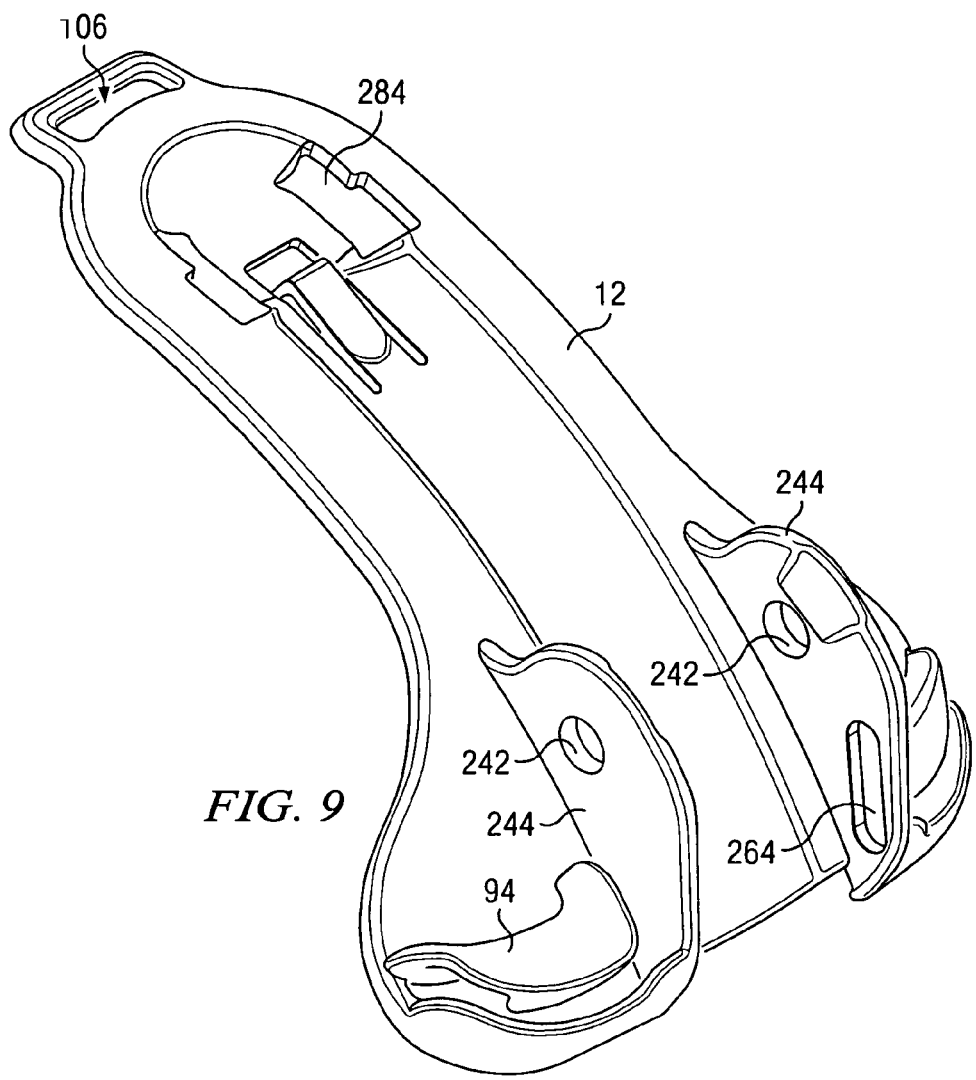
FIG. 9
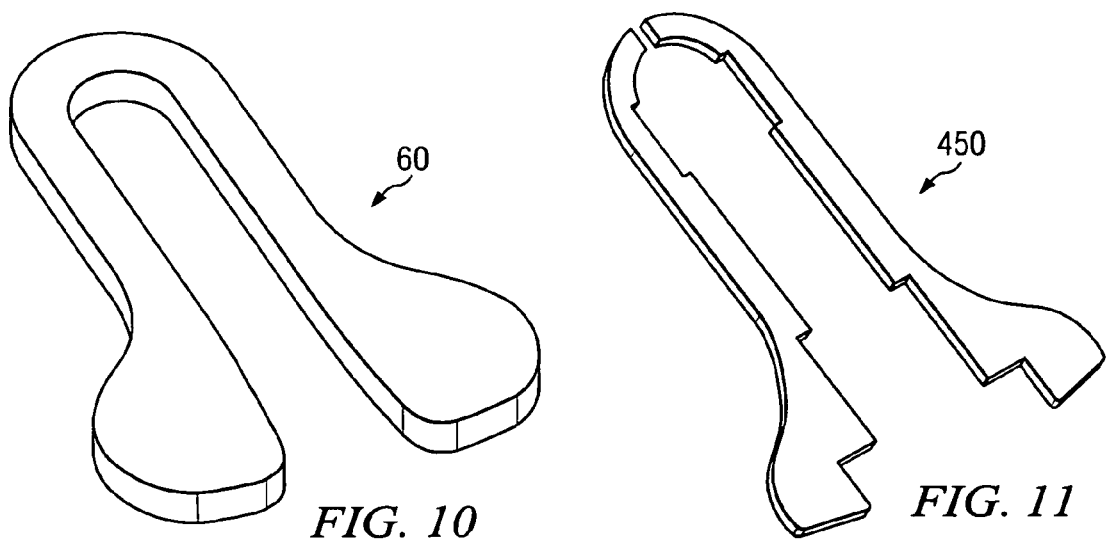
FIG. 10
FIG. 11

US 7,455,063 B2

ADJUSTABLE GAS DELIVERY MASK HAVING A FLEXIBLE GASKET

TECHNICAL FIELD

The present disclosure is related to gas delivery masks, e.g., continuous positive airway pressure (CPAP) masks, and more particularly, to an adjustable gas delivery mask having a flexible gasket.

BACKGROUND

In recent years, continuous positive airway pressure (CPAP) therapy has become a common prescription for individuals suffering from sleep apnea and/or other breathing ailments. Such therapy may involve placement of a nose or face mask on the subject during sleeping, while positive pressure air is continuously delivered to the subject through the mask. In some cases, such CPAP treatment may materially lessen the incidents and/or severity of sleep apnea, thereby allowing the subject to sleep or rest with less disturbances.

A common problem encountered with prior CPAP nose mask assemblies is the tendency to leak positive pressure air at one or more locations, such as between connections of mask assembly components and/or between the mask assembly and the subject's face, e.g., where the cheek regions and nose intersect. Leaks between the mask and the subject's face are particularly common due to the wide ranges of shapes and sizes of the heads and faces of different subjects. Leaks within a mask assembly or between the mask assembly and the subject's face may be undesirable for various reasons. For example, leaks may reduce the positive pressure of the air being delivered to the subject. As another example, leaks between the mask and the subject's face may tends to dry the subject's eyes, creating uncomfortable wearing and operating conditions. As another example, leaks may produce noises, which may be undesirable to the subject and/or the subject's bed partner. One typical way to reduce leaks is to provide a tighter compressive fit of the mask against the nose and face of the wearer. However, too tight of a fit may cause discomfort to the subject.

SUMMARY

In accordance with the present disclosure, an adjustable gas delivery mask, e.g., a continuous positive airway pressure (CPAP) mask, having a flexible gasket is provided.

In accordance with one embodiment of the present disclosure, an adjustable gas delivery system is provided. The system may include a face mask, an arm apparatus, and a gasket. The face mask may be configured to deliver gas to a subject, and may include a flexible cushion portion configured to interface with the subject's face and a rigid base portion configured to support the cushion portion, the rigid base portion including a gas inlet. The arm apparatus may be configured to deliver gas to the face mask. The arm apparatus may include a gas outlet having a cross-sectional area smaller than a cross-sectional area of the gas inlet of the base portion of the face mask. The gasket may couple the gas outlet of the arm apparatus with the gas inlet of the face mask. The gasket may be flexible such that the orientation of the face mask relative to the arm apparatus is adjustable.

In accordance with yet another embodiment of the present disclosure, a gas delivery mask apparatus is provided. The mask apparatus may include a mask body, a mask head strap, a face mask, a mask arm, and a mask gasket. The mask head strap may be configured to secure the mask body to a subject's head. The face mask may be configured to deliver gas to a subject, and may include a flexible cushion portion configured to interface with the subject's face and a rigid base portion configured to support the cushion portion, the rigid base portion including a gas inlet. The mask arm may be coupled to the mask body and configured to support the face mask and deliver gas to the face mask. The mask arm may include a gas outlet having a cross-sectional area smaller than a cross-sectional area of the gas inlet of the base portion of the face mask. The mask gasket may couple the gas outlet of the mask arm with the gas inlet of the face mask. The mask gasket may be flexible such that the orientation of the face mask relative to the mark arm is adjustable.

In accordance with yet another embodiment of the present disclosure, an adjustable gas delivery system is provided. The system may include a face interfacing means configured to deliver gas to a subject, a mask support means for delivering gas to the face interfacing means, and a gasket means coupling the gas outlet of the mask support means with the gas inlet of the face interfacing means. The face interfacing means may include a flexible cushioning means for interfacing with the subject's face and a rigid base means for supporting the cushioning means, the rigid base means including a gas inlet. The mask support means may include a gas outlet having a cross-sectional area smaller than a cross-sectional area of the gas inlet of the base means of the face interfacing means. The gasket means may be flexible such that the orientation of the face interfacing means relative to the mask support means is adjustable.

BRIEF DESCRIPTION OF THE DRAWINGS

Some embodiments of the disclosure may be understood by referring, in part, to the following description and the accompanying drawings, in which like reference numbers refer to the same or like parts, and wherein:

FIG. 6 is a three-dimensional view of a portion of a mask assembly illustrating the attachment of a face mask to an arm assembly, according to one embodiment of the disclosure;

FIG. 9 illustrates an example configuration of a mask body, according to one embodiment of the disclosure;

FIG. 10 illustrates an example configuration of a base pad, according to one embodiment of the disclosure;

FIG. 11 illustrates an example configuration of a hook and loop fastener sheet, according to one embodiment of the disclosure;

DETAILED DESCRIPTION

Selected embodiments of the disclosure may be understood by reference, in part, to FIGS. 1-27, wherein like number refer to same and like parts.

Figure 1:
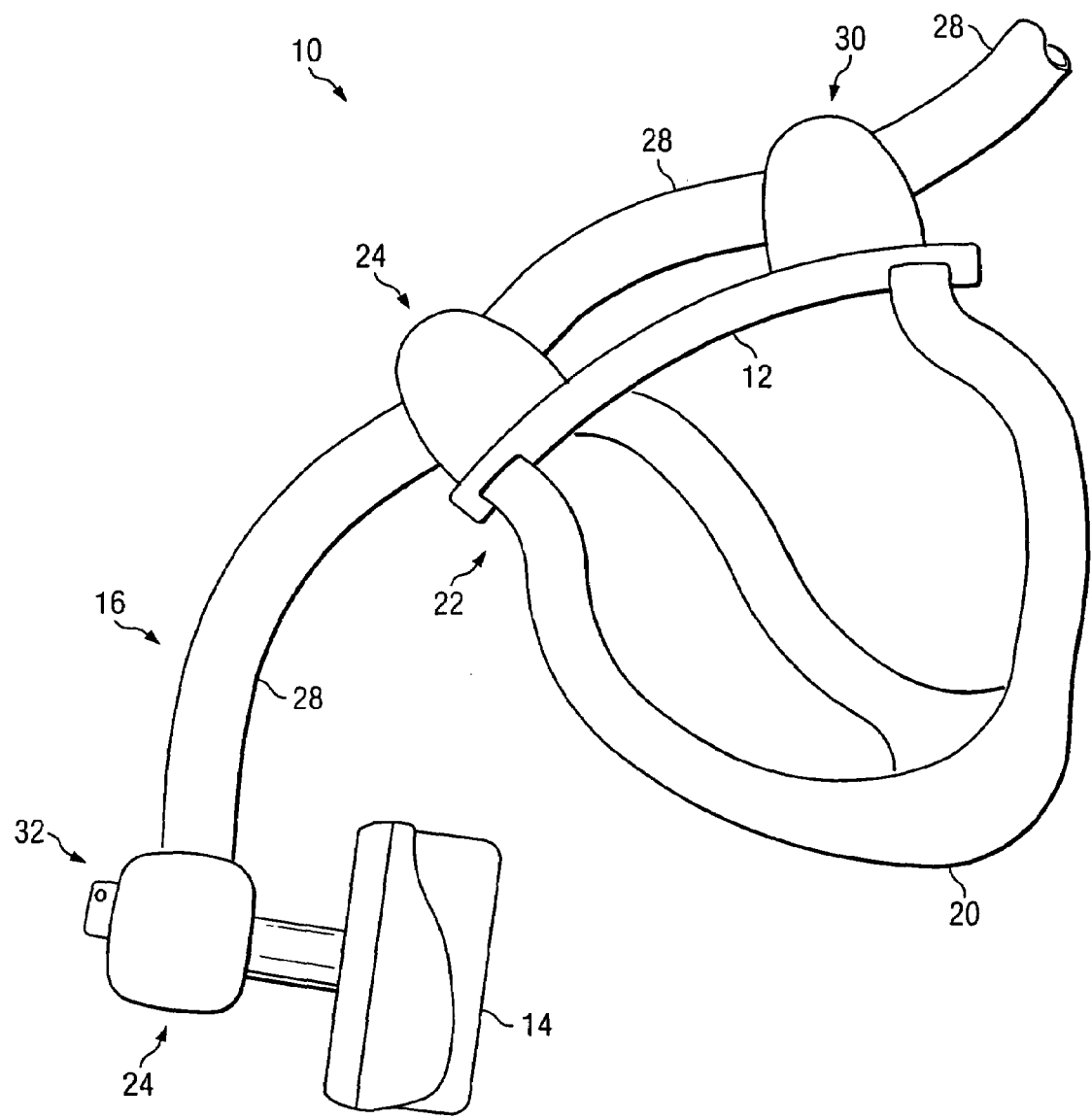
FIG. 1 illustrates a side view of a gas delivery mask apparatus, according to certain embodiments of the disclosure.

FIG. 1 illustrates a side view of a gas delivery mask apparatus 10 according to certain embodiments of the disclosure. Gas delivery mask apparatus 10 may be generally configured to assist a subject with breathing by delivering gas to the subject and/or removing gas from a subject, for example. In a particular application, mask apparatus 10 may be used to provide constant positive air pressure (CPAP) to a subject, such as to treat an apnea or other breathing condition. In certain embodiments, such as described herein, mask apparatus 10 may be secured to the subject's head.

In various embodiments, gas delivery mask apparatus 10 may include one, some or all of the following features:

(a) a mask body 12, e.g., to support mask apparatus 10 against a subject's head;

(b) a cushioned face mask 14 that may interface with the subject's face, such as around the nose and/or mouth openings;

(c) an arm assembly 16 that may support face mask 14;

(d) a head strap 20 to, e.g., secure mask apparatus 10 on the subject's head;

(e) a mask securing system 22 to, e.g., tighten and/or untighten head strap 20 around the subject's head, (f) one or more adjustment systems 24 to, e.g., adjust the position of face mask 14 against the subject's face;

(g) a gas delivery pathway 28 to, e.g., deliver one or more gases to and/or from the subject via face mask 14;

(h) a gas pathway flexibility system 30 to, e.g., provide increased flexibility to gas delivery pathway 28; and/or (i) a gas exhaust system 32 to, e.g., remove exhaled gas away from the subject.

It should be understood that in various embodiments, gas delivery mask apparatus 10 may include any combination of one, some or all of these listed features (a)-(i) and/or any one or more additional features. For example, in certain embodiments (such as the embodiment shown and discussed below with reference to FIG. 2, for example), gas delivery mask apparatus 10 may include all of the listed features (a)-(i). In another example embodiment, mask apparatus 10 may include each listed feature except feature (f). In another example embodiment, mask apparatus 10 may include each listed feature except features (e) and (h).

The one or more adjustment systems 24 to, e.g., adjust the positioning of face mask 14 against the subject's face may include one or more of the following: (a) an arm adjustment system 40 to, e.g., adjust arm assembly 16 relative to the mask body 12 and/or the subject's head, (b) a face mask adjustment system 42 to, e.g., adjust the orientation of face mask 14 relative to arm assembly 16, and (c) a gasket 44 that may provide flexibility between arm assembly 16 and face mask 14. Again, it should be understood that in various embodiments, gas delivery mask apparatus 10 may include none, one, or any combination of some or all of adjustment systems 40, 42 and 44 and/or any one or more systems for adjusting the positioning of face mask 14 against the subject's face. For example, in certain embodiments (such as the embodiment shown and discussed below with reference to FIG. 2, for example), mask apparatus 10 may include adjustment systems 40, 42 and 44. In another example embodiment, mask apparatus 10 may include arm adjustment system 40 and gasket 44, but not face mask adjustment system 42. In another example embodiment, mask apparatus 10 may include gasket 44 and face mask adjustment system 42, but not arm adjustment system 40.

Gas delivery pathway 28 may include any one or more gas delivery conduits for delivering gas to and/or from the subject via face mask 14. For example, gas delivery pathway 28 may include any one or more gas delivery conduits for delivering gas from a gas source, such as a tank, ventilator, or wall line, for example, to the subject via face mask 14. Gas delivery pathway 28 may also include one or more conduits for carrying exhaled gas away from the subject. As used herein, the term "gas" may refer to any one or more gases and/or vaporized substances suitable to be delivered to and/or from a subject via one or more breathing orifices (e.g., the nose and/or mouth), such as air, nitrogen, oxygen, any other component of air, $CO_2$, vaporized water, vaporized medicines, and/or any combination of two or more of the above, for example.

Gas pathway flexibility system 30 may include any system for providing increased flexibility to one or more components of gas delivery pathway 28. For example, in certain embodiments (such as the embodiment shown and discussed below with reference to FIG. 2, for example), gas pathway flexibility system 30 may include one or more ball joints 50 located between components of gas delivery pathway 30 to, e.g., increase the flexibility between such components.

Gas exhaust system 32 may include any system for removing exhaled gas away from the subject. For example, in certain embodiments (such as the embodiment shown and discussed below with reference to FIG. 2, for example), gas exhaust system 32 may include a gas exhaust member 52 configured to allow gas exhaled by the subject (e.g., $CO_2$) to escape from mask apparatus 10 into the surrounding environment.

In some embodiments, mask apparatus 10 may be a component of a breathing facilitation system that may facilitate or otherwise affect a subject's breathing, e.g., a CPAP system. Such a breathing facilitation system may include a mask apparatus 10, a gas (e.g., air) source, and/or one or more gas delivery conduits coupling mask apparatus 10 to the gas source such that gas may be delivered from the gas source to the subject via mask apparatus 10. The one or more gas delivery conduits may include all or portions of gas delivery pathway 28 and/or one or more addition gas delivery conduits or components for communicating gas between the gas source and mask apparatus 10. The gas source may be any device or devices configured to generate and/or supply gas (e.g., pressurized air) to a subject via mask apparatus 10. In some embodiments, the gas source may be configured to generate and/or supply pressurized gas (e.g., pressurized air) to a subject via mask apparatus 10. For example, the pressurized gas source may include a stand-alone unit capable of generating pressurized air (e.g., by pressurizing atmospheric air), a wall outlet through which pressurized air may be supplied (e.g., in a hospital or clinic), a tank of compressed air, or any other suitable source of pressurized air. In other embodiments, the gas source may be configured to generate and/or supply generally non-pressurized gas (e.g., atmospheric air), e.g., where breathing facilitation system is configured to provide clean or fresh air to a subject.

In addition, in some embodiments, the breathing facilitation system may include one or more devices to treat or condition the gas being delivered to the subject. For example, the breathing facilitation system may include one or more filters configured to filter the gas being delivered to the subject, a humidifier configured to humidify the gas being delivered to the subject, a heater or cooler configured to adjust and/or control the temperature of gas being delivered to the subject, and/or a medicine delivery device configured to deliver a medication (e.g., in vapor form) into the gas being delivered to the subject. In addition, in some embodiments, the breathing facilitation system may include a controller configured to control various parameters of the operation of the breathing facilitation system (e.g., to control various parameters of the operation of the pressurized gas source), and/or one or more sensors or other devices configured to provide feedback to the controller for regulating the operation of the breathing facilitation system. It should be understood that the breathing facilitation system may include any combination of one, some or all of the components discussed above and/or any one or more additional suitable components.

Figure 2:
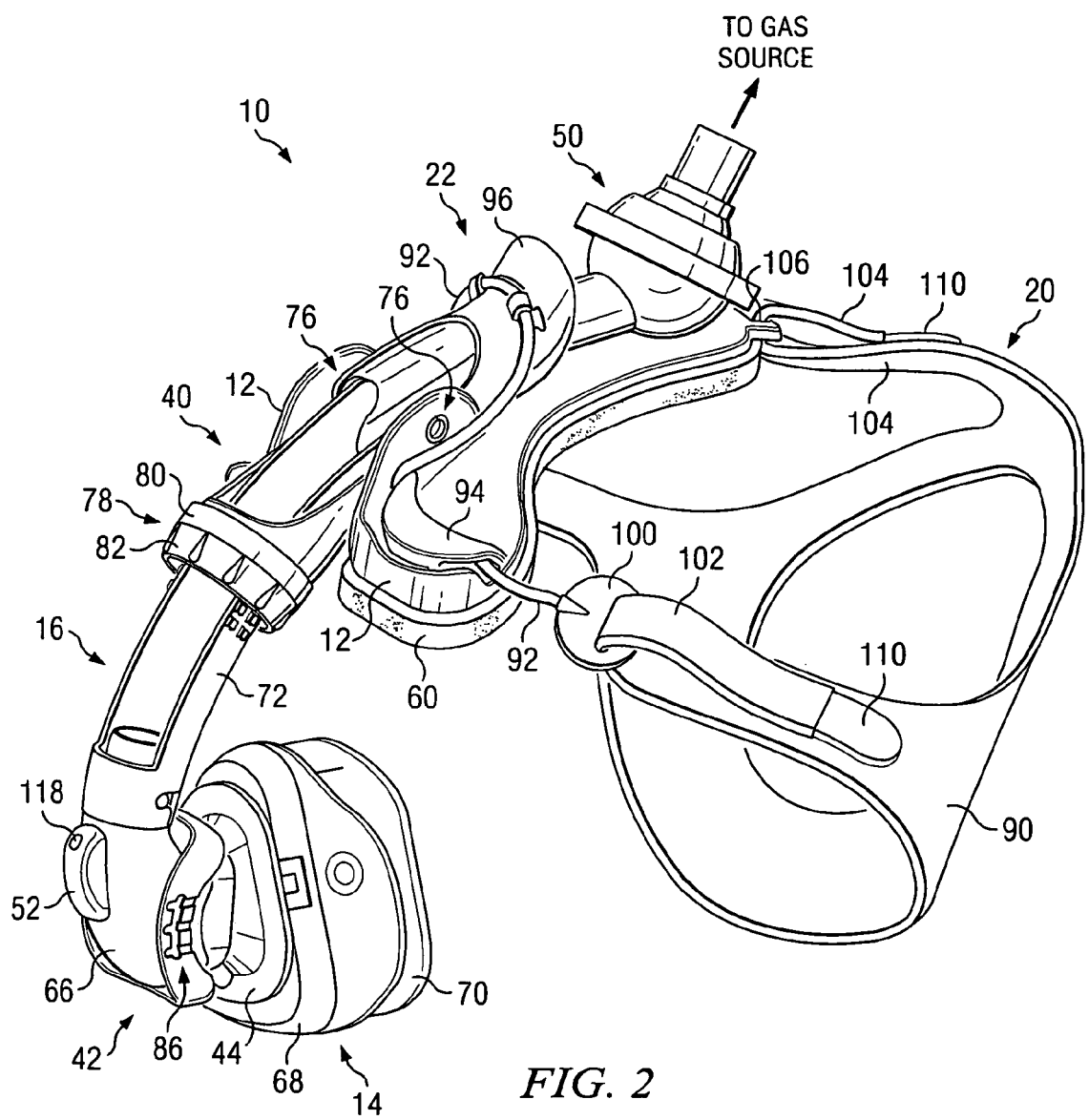
FIG. 2 illustrates a three-dimensional view of a gas delivery mask apparatus, according to one particular embodiment of the disclosure.

FIG. 2 illustrates a three-dimensional view of a gas delivery mask apparatus 10 according to one particular embodiment of the disclosure. In this particular embodiment, mask apparatus 10 may include each or any combination of the features discussed above with reference to FIG. 1. As shown in FIG. 2, mask apparatus 10 may include a mask body 12, a face mask 14, an arm assembly 16, a head strap 20, a mask securing system 22, an arm adjustment system 40, a face mask adjustment system 42, a gasket 44, a ball joint 50, a gas exhaust member 52, and/or a base pad 60.

Figure 3A:
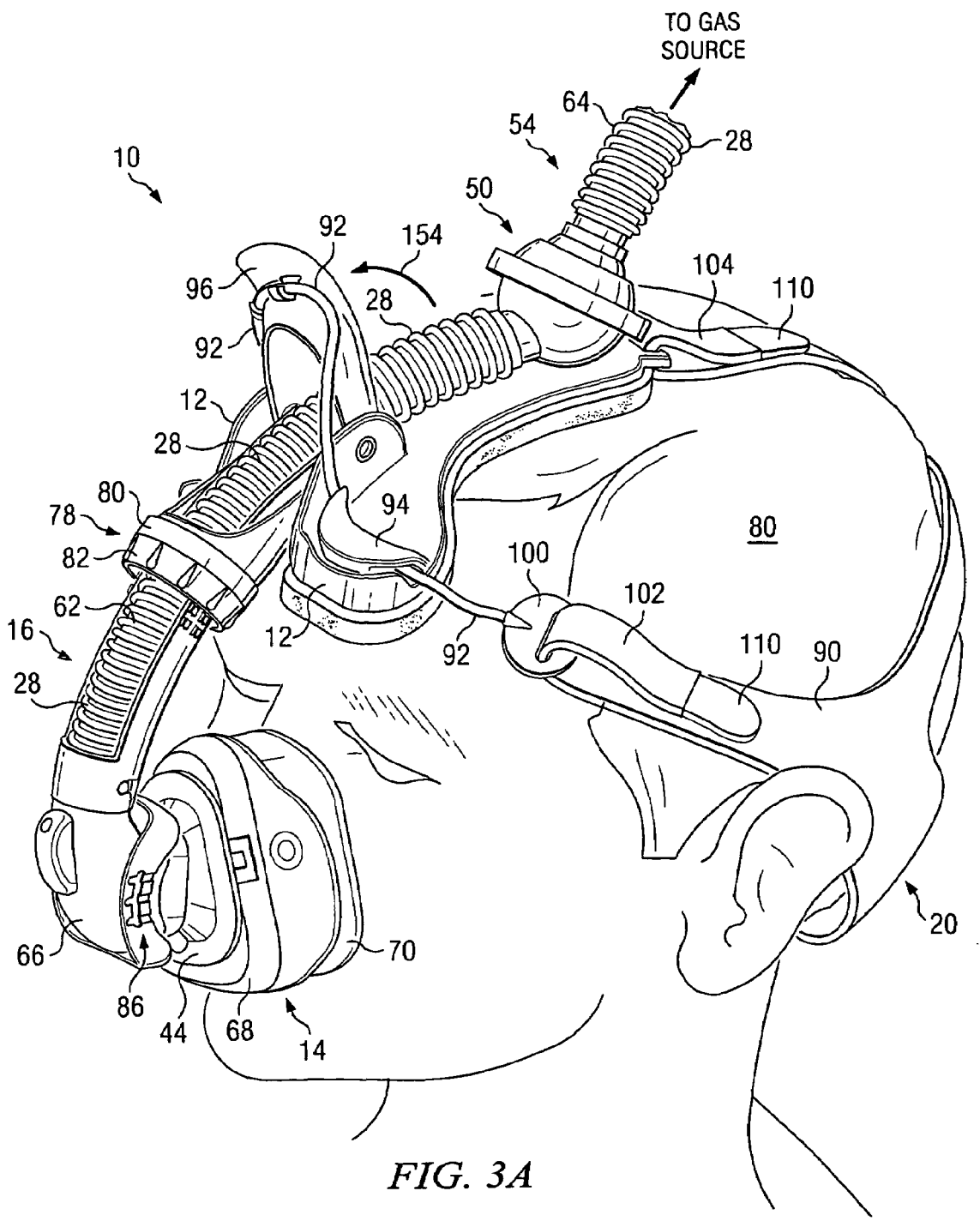
FIGS. 3A-3B illustrate a system for securing an example embodiment of a mask apparatus onto a subject's head, according to one embodiment of the disclosure.
Figure 3B:
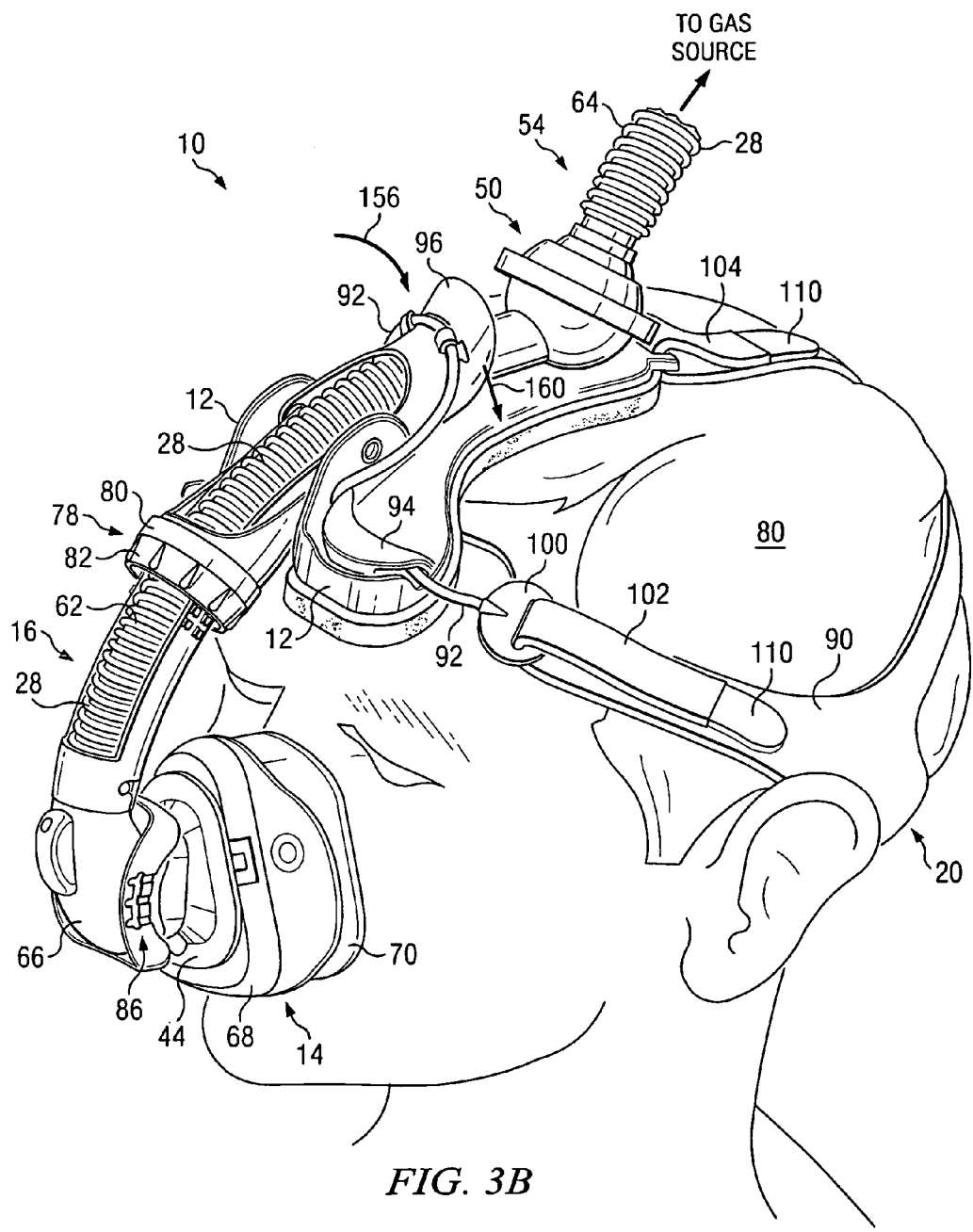

Mask apparatus 10 may also include a gas delivery pathway 28 to, e.g., deliver gas to and/or from the subject via face mask 14, which may include a first gas delivery conduit 62 generally located between a first side of ball joint 50 and face mask 14, and a second gas delivery conduit 64 extending from a second side of ball joint 50. First gas delivery conduit 62 and second gas delivery conduit 64 are shown in FIGS. 3A-3B (discussed below), but are not shown in FIG. 2 in order to better illustrate the details of and interaction between other components of mask apparatus 10. First gas delivery conduit 62 and/or second gas delivery conduit 64 may have any suitably configuration and may be formed from any suitable material for conducting gas along gas delivery pathway 28. In some embodiments, first gas delivery conduit 62 and/or second gas delivery conduit 64 may be flexible. For example, first gas delivery conduit 62 and/or second gas delivery conduit 64 may comprise flexible tubes or hoses formed from any suitably flexible material, e.g., any suitably plastic, polymer, rubber or silicone.

Mask body 12 may be generally configured to be mounted against a subject's head (e.g., the forehead) and to, e.g., support various other components of mask apparatus 10, including, e.g., arm assembly 16, head strap 20, mask securing system 22, arm adjustment system 40, and/or ball joint 50. Base pad 60 may be coupled to the underside of mask body 12 and, e.g., may provide cushioning between mask body 12 and the subject's head, which may provide increased comfort to the subject. One embodiment of a mask body 12 is illustrated and discussed in greater detail below with reference to FIG. 9.

Face mask 14 may be generally configured to be supported by arm assembly 12 and may interface with the subject's face, such as around the nose and/or mouth openings, to deliver gas to and/or remove gas from the subject. In this particular embodiment, gas may be delivered to the subject via a gas delivery pathway 28 that may include a gas source (not shown), first gas delivery conduit 62 (see FIGS. 3A-3B), ball joint 50, second gas delivery conduit 64 (see FIGS. 3A-3B), an elbow 66 of arm assembly 16, gasket 44, and/or face mask 14.

In certain embodiments, face mask 14 may include a relatively rigid base portion 68 and/or a flexible, or pliable, cushion portion 70 coupled to base portion 68. Cushion portion 70 may be shaped and/or contoured to comfortably fit against a subject's face and/or to reduce or minimize the amount of gas that escapes from between cushion portion 70 and the subject's face. For example, cushion portion may have a 3-dimensional contour designed to fit against the contours of a subject's face.

In some embodiments, cushion portion 70 may be substantially flexible or pliable. For example, cushion portion 70 may be formed from a substantially flexible or pliable plastic, polymer, or silicone. In contrast, base portion 68 may be substantially rigid relative to cushion portion 70. For example, base portion 68 may be formed from a plastic or polymer more rigid than cushion portion 70.

Arm assembly 16 may be generally configured to support and/or align face mask 14 in position against the subject's face. Arm assembly 16 may also support or be integrated with first gas delivery conduit 62, which may comprise a flexible conduit to, e.g., communicate gas between ball joint 50 and face mask 14. Arm assembly 16 may include any suitable number of distinct components. For example, in the embodiment shown in FIG. 2, arm assembly 16 may include an elongated arm member 72 coupled to elbow 66, which may include multiple distinct components.

As shown in FIG. 2, arm assembly 16 may be pivotally coupled to mask body 12 about one or more pivot points 76 such that arm assembly 16 may rotate about an axis extending laterally across mask body 12. Thus, when mask apparatus 10 is secured to a subject's head, arm assembly 16 may pivot toward or away from the subject's face, e.g., such that mask apparatus 10 may be adjusted to fit the shape and size of the subject's head and/or facial features. In addition, the subject may pivot arm assembly 16 about pivot points 76 to, e.g., control the tightness of face mask 14 against the his or her face as desired. For example, the subject may control the tightness of face mask 14 against his or her face to achieve a desired level of comfort and/or to reduce the amount of gas that escapes from between face mask 12 and the subject's face to a desirable or acceptable level. Although arm assembly 16 is shown pivotally coupled to mask body 12, in other embodiments, arm assembly 16 may be otherwise coupled to mask body 12 in any suitable manner, such as slidably, slidably and pivotally, or rigidly, or a combination of these couplings, for example.

Arm adjustment system 40 may generally be operable to control the positioning of arm assembly 16 relative to mask body 12. For example, in this embodiment, arm adjustment system 40 may include an intermediate member 78 that may be manipulated or actuated to control the rotation of arm assembly 16 relative to mask body 12 about pivot points 76. Intermediate member 78 may include any suitable number of distinct components. In the embodiment shown in FIG. 2, intermediate member 78 may include a body portion 80 and a threaded portion 82 coupled (e.g., rotatably) to body portion 80. As discussed in greater detail below with reference to FIG. 5, rotating threaded portion 82 may cause intermediate member 78 to move (e.g., slide) relative to both mask body 12 and arm member 72, which may cause arm assembly 16 to rotate relative to mask body 12, e.g., about pivot points 76. It should be understood that in other embodiments, intermediate member 78 may be otherwise configured and/or may interact differently with mask body 12 and/or arm assembly 16 to control the positioning of arm assembly 16 relative to mask body 12.

In addition, as discussed above, face mask adjustment system 42 may be provided to, e.g., adjust the orientation of face mask 14 relative to arm assembly 16. In this embodiment, face mask adjustment system 42 may include a pivot joint 86 formed in or by elbow 66 that may, e.g., allow face mask 14 to pivot upwards and/or downwards relative to arm assembly 16. Thus, face mask 14 may be pivoted as desired by the subject, such as to achieve a desired level of comfort for the subject and/or to reduce the amount of gas that escapes from between face mask 12 and the subject's face.

Gasket 44 may generally be configured to couple (e.g., flexibly couple) face mask 14 with arm assembly 16. Gasket 44 may be flexible, or pliable, to allow face mask 12 to move (e.g., rotate and/or translate) in various directions relative to arm assembly 16. In addition, gasket 44 may provide a substantially leak-free connection between face mask 12 and arm assembly 16. In this embodiment, gasket 44 may flexibly couple base portion 68 of face mask 14 with elbow 66 of arm assembly 16. However, in other embodiments, gasket 44 may otherwise couple a face mask with an arm member or assembly. The flexible coupling may provide a better and/or more versatile fit between face mask 12 and the subject's face, which may provide various advantages, such as (a) allowing mask apparatus 10 to, e.g., be used by subjects having various sized and/or shaped heads, faces, and/or facial features (e.g., noses and mouths), (b) providing increased comfort to the subject, and/or (c) reducing or eliminating the amount of gas that escapes between cushion portion 70 and the subject's face.

Relatively rigid base portion 68 of face mask 14 may provide a substantially solid base for securely and/or removably attaching gasket 44 to face mask 14. In the embodiment shown in FIG. 2, gasket 44 may include a lip which holds against an inner surface of base portion 68 such that, e.g., gasket 44 may be securely and/or removably attached to base portion 68. In other embodiments, rather than including a separate flexible cushion and rigid base portion 68, face mask 14 may comprise a single integrated structure. For example, face mask 14 may comprise a single, flexible cushion. In addition, face mask 14 may be coupled to arm assembly 16 in any other suitable manner. For example, face mask 14 may be directly coupled to arm assembly 16, or may be coupled to arm assembly 16 by another type of gasket, a flexible bellows or gusset structure, or any other flexible or rigid coupling structure or structures.

Head strap 20 may include any one or more components for securing mask apparatus 10 to a subject's head. For example, in the embodiment shown in FIG. 2, head strap 20 may include a strap portion 90 configured to wrap around the subject's head and a cord portion 92 coupled to strap portion 90 and configured to interact with a lever 96 and/or one or more strap guides 94 located on mask body 12. Strap portion 90 and/or cord portion 92 may, e.g., be formed from flexible materials. In certain embodiments, cord portion 92 may be formed from a substantially flexible material and strap portion 90 may be formed from a less flexible or inflexible material. For example, cord portion 92 may be formed from elastic or a similar material, and strap portion 90 may be formed from neoprene or a similar material.

In the embodiment shown in FIG. 2, cord portion 92 may be coupled at each end to an eyelet 100. Cord portion 92 may be coupled to eyelets 100 in any other suitable manner, such as by insert molding, for example. Each eyelet 100 may include an opening through which elongated side portions 102 of strap portion 90 may be routed. An elongated side portions 104 of strap portion 90 may be routed through an eyelet or opening 106 formed in mask body 12. Elongated portions 102 and 104 of strap portion 90 may then be folded back and coupled to strap portion 90 in any suitable manner in order to secure strap portion 90 to eyelets 100 and 106. For example, elongated portions 102 and 104 may include hook and loop fastener portions 110 that may be affixed to strap portion 90, as shown in FIG. 2. In other embodiments, strap portion 90 may be directly coupled to mask body 12, eyelets 100, and/or cord portion 92. In still other embodiments, head strap 20 comprises a single, integrated strap.

Mask securing system 22 may be generally configured to secure head strap 20 around the subject's head. In some embodiments, mask securing system 22 may be operable to tighten and/or untighten head strap 20 around the subject's head. In the embodiment shown in FIG. 2, mask securing system 22 may include mask body 12, head strap 20, and lever 96. Lever 96 may be coupled (e.g., movably coupled) to mask body 12 and generally operable to adjust head strap 20 around a subject's head, such as to tighten or loosen head strap 20 around the subject's head, for example. In the embodiment shown in FIG. 2, lever 96 may generally operate as a cinch clamp to control the tightness of head strap 20 around the subject's head. In this embodiment, lever 96 may be pivotally coupled to mask body 12 about pivot points 76, the same pivot points 76 at which arm member 72 may be pivotally coupled to mask body 12. However, in other embodiments, lever 96 and arm member 72 may be pivotally coupled to mask body 12 at different pivot points.

Head strap 20 may be coupled to lever 96 in any suitable manner, and routed though one or more strap guides 94 formed in mask body 12 such that rotation of lever 96 about pivot points 76 from an open position to a closed position (lever 96 is shown in the closed position in FIG. 2) pulls portions of head strap 20 through strap guides 94, thus tightening head strap 20 around the subject's head. In addition, head strap 20 may be retained by one or more strap retention members 114 formed in, or coupled to, lever 96. In embodiments in which head strap 20 includes a strap portion 90 and a cord portion 92, cord portion 92 may be routed through strap guides 94 and coupled to, or retained by, strap retention members 114. One embodiment of a mask securing system 22 system adjusting head strap 20 around a subject's head, including the interaction between a lever 96, a mask body 12, and a head strap 20, is illustrated and discussed in greater detail below with reference to FIGS. 3A and 3B.

Ball joint 50 may be generally configured to, e.g., provide increased flexibility for gas delivery pathway 28 (see FIGS. 3A-3B). In the embodiment shown in FIGS. 2-3B, ball joint 50 may provide additional flexibility between first gas delivery conduit 62 with second gas delivery conduit 64. Such additional flexibility may reduce the likelihood of gas delivery pathway 28 becoming crimped, tangled, or otherwise undesirably oriented during the movement of the subject, such as when the subject moves or turns his or her head during sleep, for example. One embodiment of a ball joint 50 is illustrated and discussed in greater detail below with reference to FIGS. 7A-7B.

Exhaust member 52 may be generally configured to remove exhaled gas away from the subject. In the embodiment shown in FIG. 2, exhaust member 52 may be integrated with, or coupled to, elbow 66 of arm assembly 16. For example, exhaust member 52 may be coupled to an opening in an outer surface of elbow 66. Exhaust member 52 may include an opening 118 extending though the member such that a gas passageway may be provided that extends from the open portion of face mask 14 that may interface with the subject's face, through face mask 14, gasket 44, elbow 66, and out through the opening formed in exhaust member 52. Opening 118 in exhaust member 52 may be appropriately sized to allow a desired amount of gas flow through exhaust member 52 and/or to reduce or minimize noise created by gas flowing through exhaust member 52. In addition, in some embodiments, opening 118 may be oriented at an angle relative to general direction of gas flow between elbow 66 and face mask 14, which may provide various benefits. For example, the angle of opening 118 may reduce and/or minimize the flow of exhaust gas incident upon another person, such as the subject's bed partner. One embodiment of an exhaust member 52 is illustrated and discussed in greater detail below with reference to FIGS. 19A-19B.

Base pad 60 may be generally operable to provide cushioning between mask body 12 and the subject's head, such as, e.g., proximate the subject's forehead. Base pad 60 may be formed from any suitable cushioning material, and may be coupled to mask body 12 in any suitable manner. For example, in certain embodiments, base pad 60 may be coupled to mask body 12 with hook and loop fasteners (e.g., Velcro™).

FIGS. 3A and 3B illustrate a system for securing an example embodiment of mask apparatus 10 onto a subject's head 150, according to one embodiment of the disclosure. In particular, FIG. 3A illustrates mask apparatus 10 positioned in an untightened state on a subject's head 150, and FIG. 3B illustrates mask apparatus 10 positioned in a tightened state on the subject's head 150.

As shown in FIG. 3A, head strap 20 may be positioned around the subject's head 150. Lever 96 is shown in an open, or untightened, position. As a result, head strap 20 may be relatively loose or lax around the subject's head, such that mask apparatus 10 is not tightly secured on the head 150 and may thus be relatively easily removed from the head 150. Lever 96 may be rotatable relative to mask body 12 about pivot points 76. In this particular embodiment, lever 96 is in the open position when rotated downward toward face mask 14, as indicated by arrow 154. Rotating lever 96 downward toward the open position (from the closed position shown in FIG. 4B) may shorten the distance between strap guides 94 on mask body 12 and the point(s) at which cord portion 92 of head strap 20 is coupled to lever 96. Thus, rotating lever 96 downward toward the open position may allow strap portion 90 of head strap 20 to pull away from mask body 12, thus untightening head strap 20 around head 150.

In contrast, as shown in FIG. 3B, lever 96 is shown in the closed, or tightened, position. As a result, head strap 20 may be relatively tight around the subject's head, such that mask apparatus 10 may be substantially secured on the head 150. In this embodiment, lever 96 is in the closed position when rotated upward toward the top of mask body 12 and ball joint 50, as indicated by arrow 156. Rotating lever 96 upward toward the closed position (from the open position shown in FIG. 3A) may increase the distance between strap guides 94 on mask body 12 and the point(s) at which cord portion 92 of head strap 20 is coupled to lever 96. Thus, rotating lever 96 upward toward the closed position may pull strap portion 90 toward mask body 12, which may tighten head strap 20 around head 150. In other words, lever 96 may act as a cinch clamp or lever to tighten head strap 20 around head 150.

In some embodiments, tension within head strap 20 may act to hold lever 96 in the closed position, as opposed to pulling lever 96 toward the open position. For example, as shown in the embodiments of FIGS. 1-2, cord portion 92 of head strap 20 may pass by pivot points 76 on the side closer to mask body 12 and the subject's head 150. In other words, at the point where cord portion 92 passes by pivot points 76, pivot points 76 are located further from the subject's head 150 than cord portion 92. Thus, tension on cord portion 92 creates a moment on lever 96 in a direction toward mask body 12 and the subject's head 150, as indicated by arrow 160 in FIG. 3B. Thus, the greater the tension in head strap 20, the greater the moment on lever 96 forcing lever 96 toward (or retaining lever 96 in) the closed position. Such configuration may thus reduce the likelihood of lever 96 of moving to the open position without the subject manually pulling lever 96 to the open position (at least when mask apparatus 10 is being worn by a subject).

As shown in FIGS. 3A-3B, one or more adjustments may be made to mask apparatus 10 to position face mask 14 comfortably against the subject's face and/or to reduce leaks between face mask 14 and the subject's face. For example, as discussed above, arm assembly 16 may be pivotally coupled to mask body 12 at pivot points 76 such that arm assembly 16 may be rotated toward and away from the subject's face to a desired position. Arm assembly 16 may be pivoted relative to mask body 12 by rotating threaded portion 82 of intermediate member 78, as discussed below with reference to FIG. 5. In addition, face mask 14 may be pivoted upward and/or downward relative to arm assembly 16 at pivot joint 86, as desired by the subject. Also, head strap 20 may be adjusted to fit the particular subject's head 150. For example, elongated side portions 102 and/or elongated side portions 104 of strap portion 90 may be adjusted by un-securing and re-securing hook and loop fastener portions 110 at different locations.

Figure 4:
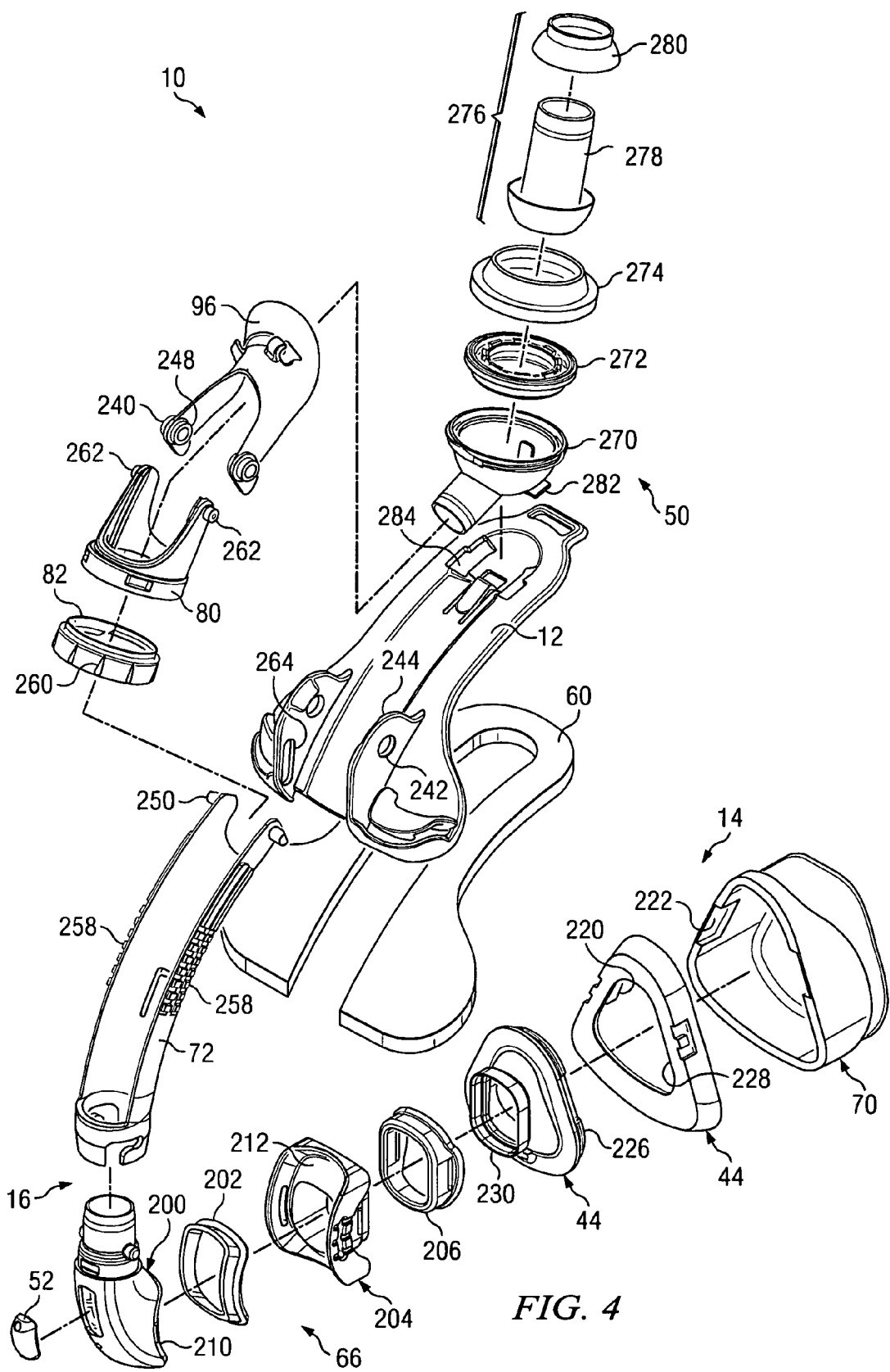
FIG. 4 illustrates a three-dimensional exploded view of a mask apparatus, according to one particular embodiment of the disclosure.

FIG. 4 illustrates a three-dimensional exploded view of mask apparatus 10 (except for head strap 20), according to one particular embodiment of the disclosure. In this embodiment, mask apparatus 10 includes mask body 12, face mask 14, arm assembly 16, head strap 20, gasket 44, ball joint 50, base pad 60, intermediate member 78, and lever 96.

Mask body 12 may support arm assembly 16, ball joint 50, and/or intermediate member. Arm assembly may include arm member 72 and elbow 66. Elbow 66 may include exhaust member 52, front elbow portion 200, slider seal 202, rear elbow portion 204, and clip 206. Exhaust member 52 may be coupled to an opening in front elbow portion 200. Slider seal 202 may generally be received within a first side of front elbow portion 200 and such that slider seal 202 forms a seal between a rear surface 210 of front elbow portion 200 and a front surface 212 of rear elbow portion 204. Slider seal 202 may thus reduce or eliminate gas leaking out from between front elbow portion 200 and rear elbow portion 204. Slider seal 202 may be formed from any suitable sealing material, such as rubber or a flexible polymer, for example.

Rear elbow portion 204 may be coupled to front elbow portion 200 such that rear elbow portion 204 may slide relative to front elbow portion 200. In some embodiments, rear surface 210 of front elbow portion 200 and/or front surface 212 of rear elbow portion 204 are curved such that rear elbow portion 204 may slide through an arc relative to front elbow portion 200. Thus, as rear elbow portion 204 slides through the arc, rear elbow portion 204 rotates relative to front elbow portion 200, such that face mask 14, which may be coupled (directly or indirectly) to rear elbow portion 204, rotates relative to arm member 72. Clip 206 may be coupled to rear elbow portion 204 in any suitable manner, such as by clipping onto rear elbow portion 204, for example.

As discussed above, face mask 14 may include relatively rigid base portion 68 and relatively flexible, or pliable, cushion portion 70. Base portion 68 may be coupled to cushion portion 70 in any suitable manner, such as by clips, adhesive, or fasteners, for example. In the embodiment shown in FIG. 4, base portion 68 includes a number of tabs 220 proximate an outer perimeter of base portion 68 and extending toward cushion portion 70. Tabs 220 may be received and locked into place in slots 222 formed proximate an outer perimeter of cushion portion 70. Once locked together, base portion 68 may be separated from cushion portion 70 by squeezing cushion portion 70 proximate each of tab 220/slot 222 interface such that each tab 220 is released from its corresponding slot 222. In another embodiment, cushion portion 70 includes a number of tabs proximate an outer perimeter of cushion portion 70 and extending toward base portion 68. Such tabs may be received and locked into place in slots formed proximate an outer perimeter of base portion 68. Similar to the previous embodiment discussed above, once locked together, base portion 68 may be separated from cushion portion 70 by squeezing cushion portion 70 proximate each of tab/slot interface such that each tab is released from its corresponding slot.

As discussed above, face mask 14 may be coupled to elbow 66 by gasket 44. In this embodiment, gasket 44 may include a first lip 226 that attaches to an opening 228 formed in base portion 68 of face mask 14, and a second lip 230 that may be held in place between (e.g., wedged between) an outer surface of rear elbow portion 204 and an inner surface of clip 206, as shown in greater detail and discussed below with reference to FIG. 6.

As discussed above, both arm member 72 and lever 96 may be pivotally coupled to mask body 12. In this embodiment, both arm member 72 and lever 96 are pivotally coupled to mask body 12 at the same pivot points 76. Lever 96 may be substantially U-shaped and may include a pair of lever pegs 240, one on each side, that may be disposed within pivot holes 242 formed in side walls f of mask body 12. Thus, lever 96 may pivot relative to mask body 12 about pivot points 76. Each lever peg 240 may have a hole 248 formed therein. Each hole 248 may or may not be concentric with the outer surface of its respective lever peg 240. Arm member 72 may include a pair or arm pegs 250, one on each side, that may be disposed within holes 248 formed in lever pegs 240. Thus, when lever 96 and arm member 44 are assembled onto with mask body 12, arm pegs 250 may rotate within holes 248 formed in lever pegs 240, which lever pegs 240 may rotate within pivot holes 242 formed in mask body 12. In this manner, both arm member 72 and lever 96 may be pivotally coupled to mask body 12 at pivot points 76.

As used herein, the term "hole" may refer to any notch, slot, or other indention of any shape or size and that may extend completely or only partially through the relevant element. Thus, for example, pivot holes 242 may extend partially or completely through the thickness of side walls 244.

As discussed above, intermediate member 78 may include body portion 80 and threaded portion 82 coupled (e.g., rotatably) to body portion 80. As shown in FIG. 4, base portion may be U-shaped and may have a circular end that may be coupled (e.g., rotatably) with threaded portion 82. Threaded portion 82 may be ring-shaped and may have one or more threads formed on an inner surface. Threaded portion 82 may also include grips 260 on an outer surface that may provide the subject a better grip for rotating threaded portion 82 in order to pivot arm assembly 16. Grips 260 may include any shape or configuration of the outer surface of threaded portion 82 and/or any material that may provide increased friction for facilitating the rotation of threaded portion 82. Intermediate member 78 may be disposed around arm member 72 such that arm member extends through the ring-shaped openings in both body portion 80 and threaded portion 82. The thread(s) formed on the inner surface of threaded portion 82 may interface with a series of threads 258 formed on the outer surface of arm member 72.

Body portion 80 may include a pair of intermediate member pegs 262, one on each side, each configured to be disposed in a notch 264 formed in side walls 244 of mask body 12. As used herein, the term "notch" may refer to any hole, notch, slot, or other indention of any shape or size and that may extend completely or only partially through the relevant element. In certain embodiments, each notch 264 may be an elongated opening appropriately sized and shaped to guide intermediate member pegs 262 within and along such elongated openings. For example, each notch 264 may have an elongated linear or curved shape. When mask apparatus 10 is assembled, rotation of threaded portion 82 causes intermediate member 78 to slide relative to arm member 72, which in turn causes intermediate member pegs 262 slide within and along notches 264, which in turn forces arm member 72 to pivot relative to mask body 12 about pivot points 76. Such interaction between intermediate member 78, arm member 72, and mask body 12 in a particular embodiment of the disclosure is illustrated and discussed in greater detail below with reference to FIG. 5.

As discussed above, mask body 12 may also support ball joint 50, which may provide flexibility between portions of gas delivery pathway 28, such as between first gas delivery conduit 62 and second delivery conduit 64 (e.g., see FIG. 2). Ball joint 50 may include any number of components arranged in any suitable manner to provide a flexible joint between portion of gas delivery pathway 28.

In the embodiment shown in FIG. 4, ball joint 50 includes a bottom housing 270, a seal/spring 272, a top housing 274, and a ball 276. Ball 276 may include a ball body 278 and a ball cap 280. Ball body 278 may include a hollow cylinder and a hemispherical portion extending from a first end of the cylinder. Ball cap 280 may comprise a hemispherical portion having an opening configured to receive the hollow cylinder of ball body 278 and configured to abut the hemispherical portion of ball body 278 such that the hemispherical portions of ball body 278 and ball cap 280 form a ball having a passage extending through the ball. However, in other embodiments, ball 276 may comprise a single or integrated component.

Bottom housing 270 may attach to mask body 12. For example, as shown in FIG. 4, bottom housing 270 may include one or more tabs 282 that slide into one or more notches 284 formed in mask body 12 such that bottom housing 270 may be removably coupled to mask body 12. However, in other embodiments, bottom housing 270 may be otherwise coupled to mask body 12, or may not be coupled to mask body 12. Seal/spring 272 may be disposed within and/or coupled to bottom housing 270 in any suitable manner. In some embodiments, seal/spring 272 may include a flexible ring integrated with, or coupled to, a seal ring. Ball 276 may be disposed against the seal ring of seal/spring 272 such that the seal ring may provide a first seal against the outer surface of ball 276. Top housing 274 may then be positioned over ball 276 such that the cylindrical portion of ball body 278 extends through an opening in top housing 274. Top housing 274 may be coupled to bottom housing 270 in any suitable manner in order to complete the assembly. For example, an edge of top housing 274 may screw onto an edge of bottom housing 270. Once assembled, an interior surface of top housing 274 acts as a second seal against the outer surface of ball 276. The assembly and operation of a particular embodiment of a ball joint 50 are illustrated and discussed in greater detail below with reference to FIGS. 7A-7B.

Figure 5:
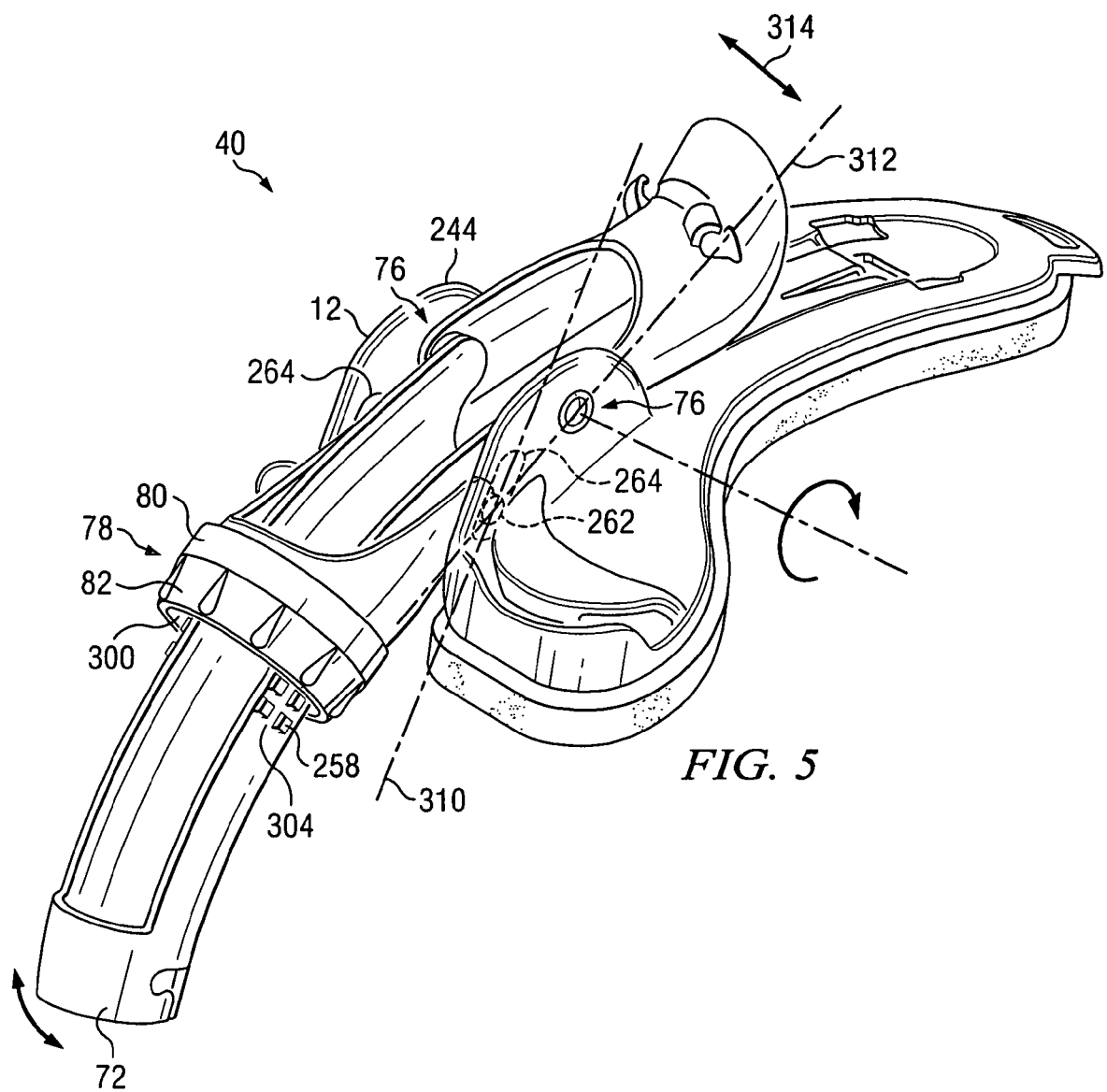
FIG. 5 is a three-dimensional view of a portion of a mask assembly illustrating an arm adjustment system, according to one embodiment of the disclosure.

FIG. 5 is a three-dimensional view of a portion of a mask assembly 10 illustrating an arm adjustment system 40 according to one embodiment of the disclosure. In this particular embodiment, arm adjustment system 40 may include an intermediate member 78 that may be manipulated or actuated to control the rotation of arm member 72 relative to mask body 12 about pivot points 76. Intermediate member 78 may include body portion 80 and threaded portion 82 coupled (e.g., rotatably) to body portion 80. Body portion 80 may include a pair of intermediate member pegs 262, each disposed in a notch 264 formed in a sidewall 244 of mask body 12 such that intermediate member pegs 262 may slide within notches 264 to allow body portion 80 to slide or otherwise move relative to mask body 12.

Figure 16:
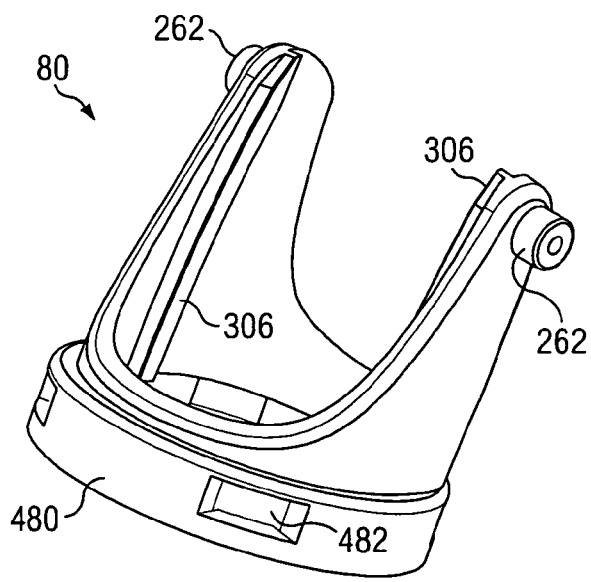
FIG. 16 illustrates an example configuration of a body portion of an intermediate member, according to one embodiment of the disclosure.
Figures 15A, 15B:
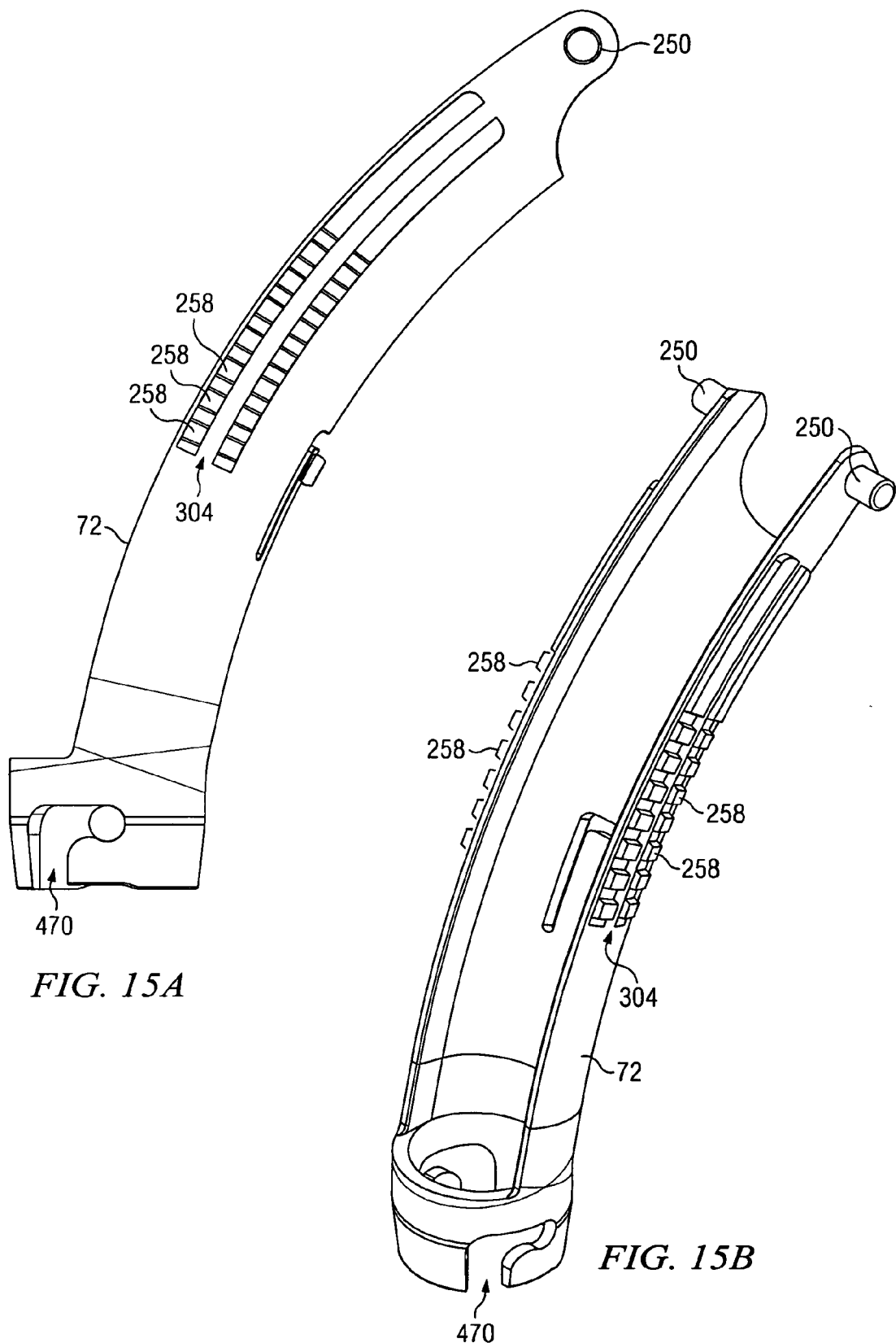
FIGS. 15A-15B illustrate an example configuration of an arm member, according to one embodiment of the disclosure.

Threaded portion 82 may be ring-shaped and may include one or more threads 300 formed on an interior surface of the ring. These threads may be threaded with one or more threads 258 formed on an outer surface of arm member 72. As used herein, "threads" may refer to one or more ribs or notches extending partially or completely around a surface. In this embodiment, threads 258 may comprise ribs extending a relatively short portion of the distance around an outer surface of arm member 72. A series of threads 258 may be formed on opposing sides of arm member 72. In addition, a notch 304 may extend across and through each series of threads 258. Each notch 304 may be configured to guide a guide member 306 formed on an interior surface of body portion 80 along arm member 72 as intermediate member 78 slides along arm member 72, as discussed below. One embodiment of an arm member 72, including an example configuration of threads 258 and notches 304, is shown in FIGS. 15A-15B. In addition, one embodiment of a body portion 80 of an intermediate member 78, including an example configuration of guide member 306, is shown in FIG. 16.

In order to actuate arm adjustment system 40, threaded portion 82 of intermediate member 78 may be rotated relative to body portion 80. As threaded portion 82 is rotated, threads 258 on body portion 80 interact with threads 258 on arm member 72, which causes intermediate member 78 to slide along the length of arm member 72. In this embodiment, since arm member 72 may be pinned to mask body 12 at pivot points 76, as intermediate member 78 slides along the length of arm member 72, intermediate member 78 may slide relative to mask body 12 and intermediate member pegs 262 may slide within notches 264. Thus, the orientation of notches 264 may control the direction that intermediate member 78 slides relative to mask body 12.

In certain embodiments, notches 264 are elongated and extend in a first direction 310 having an angular offset from an axis 312 defined by a line extending through one of the pivot points 76 and the center point of the notch 264 on the same the same side of mask body 12. For example, in this embodiment, notches 264 extend in a first direction 310 having an angular offset in the direction of axis 314 (perpendicular to axis 312) from axis 312. Axis 314 may thus extend generally perpendicular to the surface of the subject's head (when mask assembly 10 is worn on the head) at a point proximate pivot points 76. In certain embodiments, first direction 310 may be offset in the direction of the axis 314 from axis 312 by about 20 degrees to about 70 degrees. In a particular embodiment, first direction 310 may be offset in the direction of the axis 314 from axis 312 by about 45 degrees.

Because notches 264 extend in a direction offset from axis 312, as intermediate member pegs 262 slide along notches 264 in direction 310, intermediate member 78 forces arm member 72 to rotate about pivot points 76. In some embodiments, actuation of intermediate member 78 may rotate arm member 72 through an approximately 20 degree range of motion. In other embodiments, arm member 72 may be rotated through a range of motion more or less than 20 degrees.

The rotation of arm member 72 may force intermediate member 78 to rotate about intermediate member pegs 262. Thus, in this embodiment, rotating threaded portion 82 may cause intermediate member 78 to simultaneously slide and rotate relative to mask body 12. In addition, as intermediate member 78 slides along arm member 72, each guide member 306 formed on an interior surface of body portion 80 may slide within and along a corresponding notch 304 extending across and through threads 258. Guide members 306 and notches 304 may help maintain body portion 80 of intermediate member 78 properly oriented with respect to arm member 72, which may facilitate the sliding of intermediate member 78 relative to arm member 72.

FIG. 6 is a three-dimensional view of a portion of a mask assembly 10 illustrating the attachment of a face mask 14 to an arm assembly 16 according to one embodiment of the disclosure. In this particular embodiment, such portion of mask assembly 10 includes a face mask adjustment system 42 generally configured for adjusting the orientation of face mask 14 relative to arm assembly 16, such as to provide increased comfort to the subject and/or reduced leakage of gas between face mask 14 and the subject's face.

As shown in FIG. 6, elbow 66 may include front elbow portion 200, rear elbow portion 204, and clip 206. Front elbow portion 200 may include a pair of guide members 340, one extending from each side of front elbow portion 200. Rear elbow portion 204 may include a pair of guide notches 342, one formed in each side of rear elbow portion 204. Guide notches 342 may be curved or arced. Rear elbow portion 204 may be coupled to front elbow portion 200 such that guide members 340 are positioned in guide notches 342. In one embodiment, guide members 340 snap into guide notches 342, which thereby couples rear elbow portion 204 to front elbow portion 200.

Rear elbow portion 204 may be coupled to front elbow portion 200 such that rear elbow portion 204 may slide relative to front elbow portion 200. Since guide notches 342 may be curved or arced, as guide members 340 slide along guide notches 342, rear elbow portion 204 may slide through an arc relative to front elbow portion 200. In addition, rear surface 210 of front elbow portion 200 (see, e.g., FIG. 18B) and/or front surface 212 of rear elbow portion 204 (see, e.g., FIG. 21A) may be curved to allow rear elbow portion 204 to slide through an arc relative to front elbow portion 200.

As rear elbow portion 204 slides through an arc relative to front elbow portion 200, rear elbow portion 204 rotates relative to front elbow portion 200, such that face mask 14, which may be coupled to rear elbow portion 204 as discussed below, rotates relative to elbow 66 (and thus relative to arm member 72).

Gasket 44 may be coupled to elbow 66 using clip 206. For example, second lip 230 of gasket 44 may be secured between an outer surface 350 of rear elbow portion 204 and an inner surface 352 of clip 206. In one embodiment, gasket 44 may be wedged between outer surface 350 and inner surface 352. However, gasket 44 may be otherwise coupled to rear elbow portion 204 and/or clip 206. Clip 206 may be coupled to rear elbow portion 204 in any suitable manner. For example, clip 206 may be clipped onto rear elbow portion 204 by clipping one or more clip tabs 354 formed on rear elbow portion 204 into one or more clip notches 356 formed in clip 206. Gasket 44 may be coupled to face mask 14 in any suitable manner. For example, first lip 226 of gasket may attach to an opening 228 formed in base portion 68 of face mask 14, such that a base flange 358 of gasket 44 may be disposed against a front surface 359 of base portion 68 to help form a seal between gasket 44 and base portion 68.

Figure 7A:
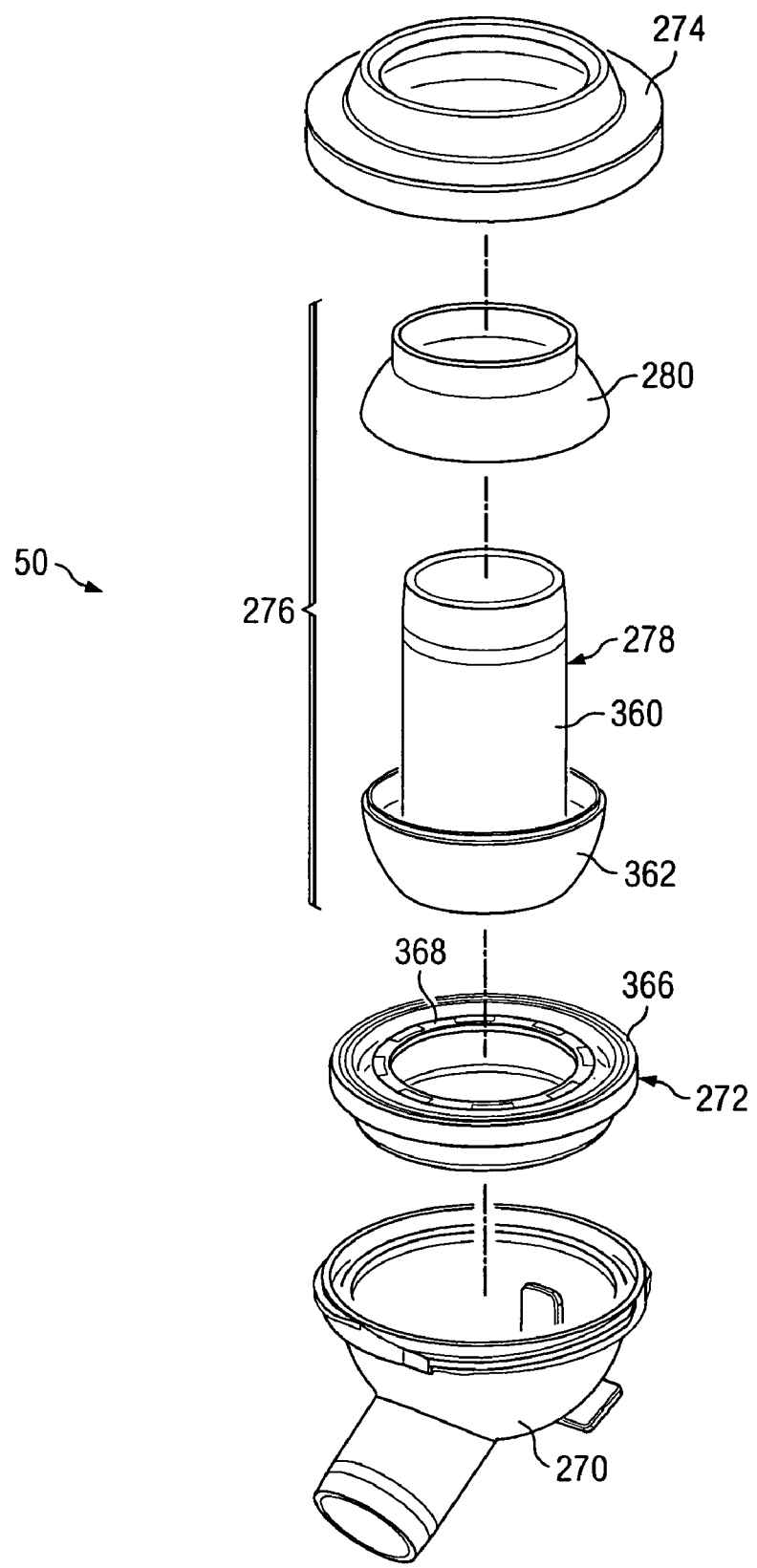
FIGS. 7A-7B illustrate an example ball joint for providing flexibility to a gas delivery pathway, according to one embodiment of the disclosure.
Figure 7B:
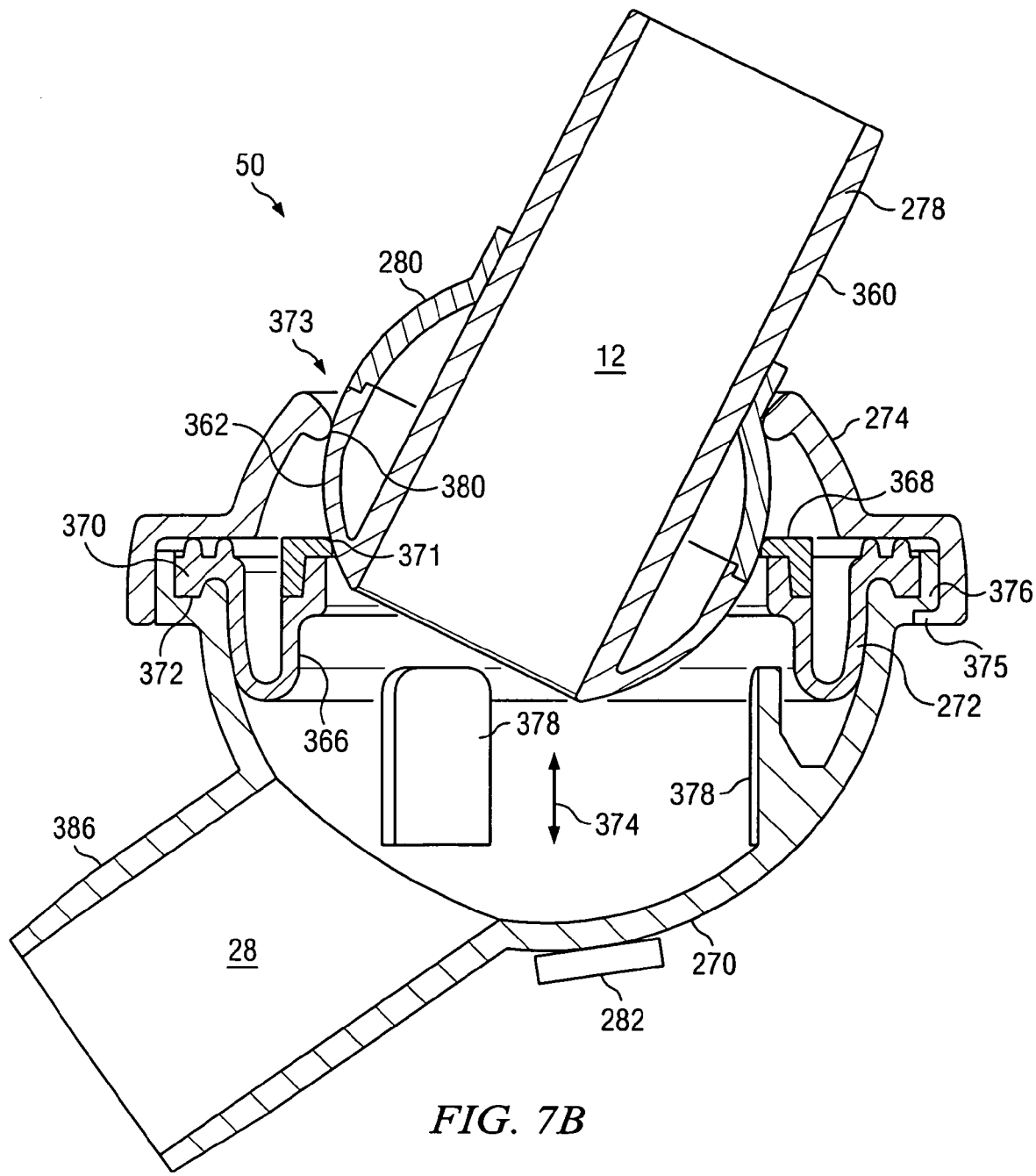

FIGS. 7A and 7B illustrate an example ball joint 50 according to one embodiment of the disclosure. In particular, FIG. 7A is a three-dimensional exploded view of ball joint 50, and FIG. 7B is a cross-sectional view of ball joint 50 according to one embodiment.

As shown in FIGS. 7A and 7B, ball joint 50 may include bottom housing 270, seal/spring 272, top housing 274, and a ball 276. Ball 276 may include a ball body 278 and a ball cap 280. Ball body 278 may include a hollow cylinder portion 360 and a hemispherical portion 362 extending from a first end of cylinder portion 360. Hollow cylinder portion 360 may have a continuous cylindrical inner surface. Ball cap 280 may have a hemispherical shape having an opening configured to receive hollow cylinder portion 362 of ball body 278 and configured to abut hemispherical portion 362 of ball body 278 to form a ball having a passage extending through the ball.

Figure 24A:
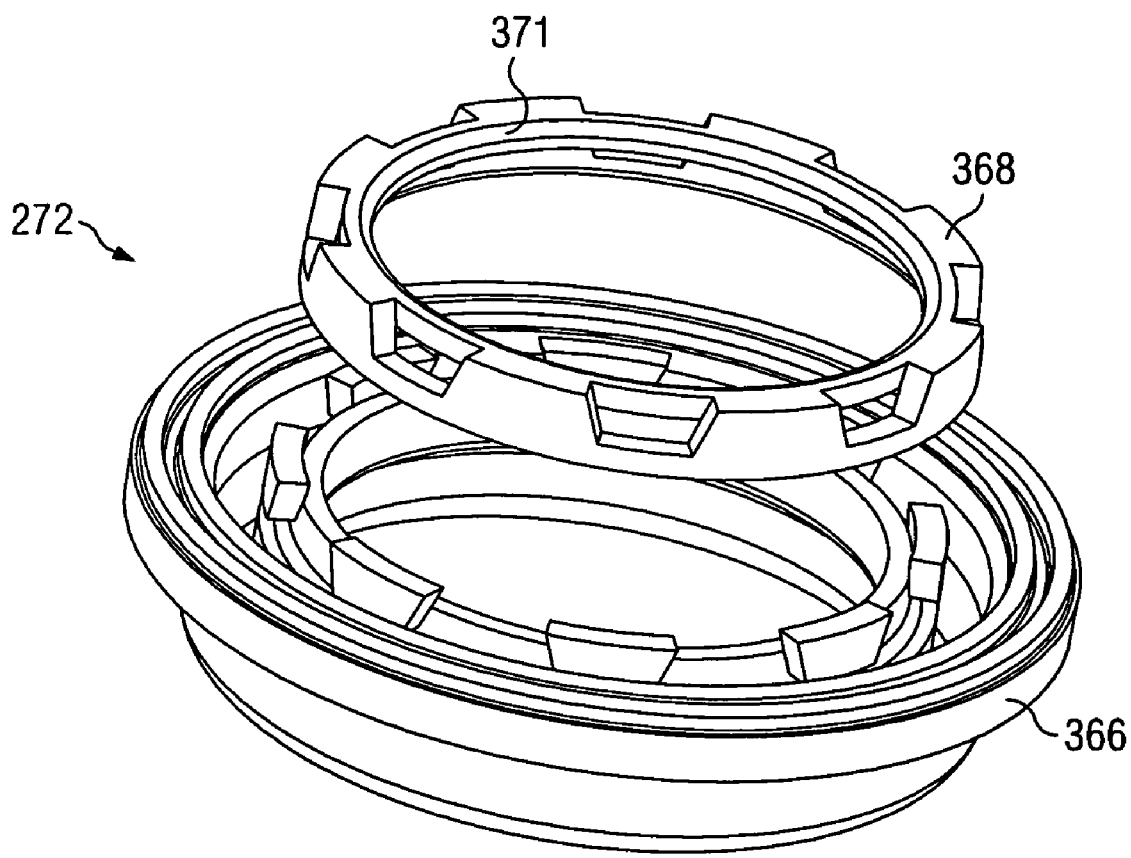
FIGS. 24A-24B illustrate an example configuration of a seal/spring, according to one embodiment of the disclosure.
Figure 24B:
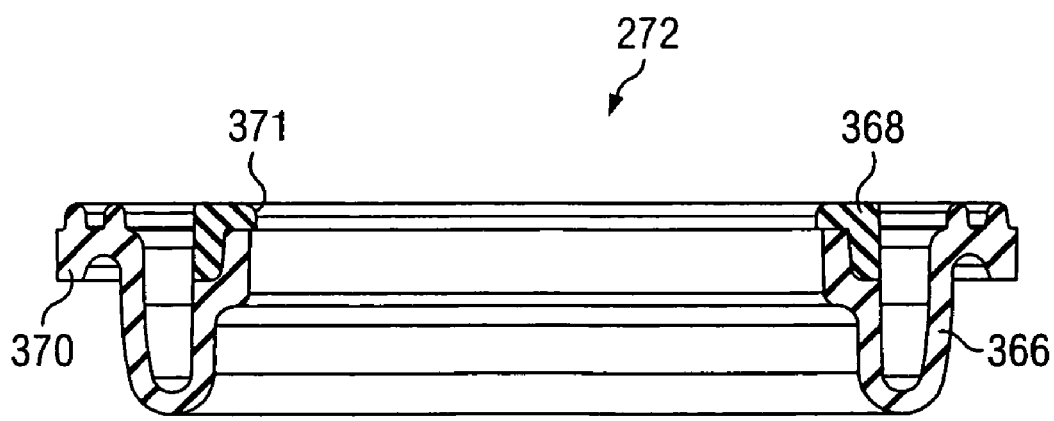

Seal/spring 272 may include a flexible ring 366 integrated with, or coupled to, a seal ring 368 in any suitable manner. For example, in one embodiment, flexible ring 366 and seal ring 368 are molded together to form an integrated component. One example embodiment of a seal/spring 272 assembly is shown in FIGS. 24A-24B. Flexible ring 366 may be disposed within, or coupled to, bottom housing 270 in any suitable manner such that seal ring 368 may be suspended from contacting bottom housing 270. For example, flexible ring 366 may include a lip 370 that may rest against an edge 372 of bottom housing 270. Because ring 366 may be flexible and may suspend seal ring 368 from contacting bottom housing 270, seal ring 368 may move up and down relative to bottom housing 270, i.e., in the direction indicated by arrow 374. In some embodiments, bottom housing 270 may include one or more stops 378 configured to limit the distance that seal ring 368 may move toward the bottom of bottom housing 270. For example, bottom housing 270 may include three or more stops 378 located around an inner perimeter of bottom housing 270.

Seal ring 368 may be configured to interface with ball 276, as discussed below. Thus, seal ring 368 may have a desirable coefficient of friction, which may be lower than that of flexible ring 366. In other words, flexible ring 366 may be configured to provide a desired amount of flexibility and/or provide a desired amount of resiliency to resist seal ring 368 being pushed toward the bottom of bottom housing 270, whereas seal ring 368 may be configured to provide a seal and/or a desired level of friction against ball 276. In certain embodiments, flexible ring 366 may be formed from an elastic material, such as a rubber or polymer, and seal ring 368 may be formed from a more rigid material, such as a more rigid polymer, for example.

As shown in FIG. 7B, ball 276 may be disposed against an inner surface, or rim, 371 of seal ring 368 such that ball 276 may rotate relative to seal ring 368. Top housing 274 may then be positioned over ball 276 such that hollow cylindrical portion 360 of ball body 278 extends through an opening 373 in top housing 274. Top housing 274 may be secured to bottom housing 270 in any suitable manner in order to complete the assembly. For example, a thread or lip 375 of top housing 274 may screw onto a thread or lip 376 of bottom housing 270.

When restrained by top housing 274, ball 276 forces seal ring 368 downward toward bottom of bottom housing 270 due to the size of ball 276. Flexible ring 366 flexes to allow such movement of seal ring 368, but provides resiliency to resist such flexing such that the resiliency of flexible ring 366 may press seal ring 368 upwardly against ball 276, thus maintaining rim 371 of seal ring 368 in contact against ball 276. Such interface between rim 371 and ball 276 may act as a seal between rim 371 and ball 276, which may prevent or resist gas leakage from gas delivery pathway 28 (particularly, from a portion of gas delivery pathway 28 defined by bottom housing 270). As discussed above, seal ring 368 may be formed from a suitable material providing a desired level of friction against ball 276 in order to allow ball 276 to rotate with a desired level of freedom or resistance.

In addition, the resiliency of flexible ring 366 may force ball 276 upward against a rim 380 associated with top housing 274. In this embodiment, rim 380 may be defined by top housing 274. In other embodiments, rim 380 may be provided by a separate component coupled to or otherwise associated with top housing 274.

Such interface between rim 380 and ball 276 may act as a seal between rim 380 and ball 276, which may prevent or resist gas leakage from gas delivery pathway 28. For example, the seal between rim 380 and ball 276 may prevent or resist the leakage of gas from a volume defined by seal/spring 272 and top housing 274. Thus, this seal may act as a second seal to prevent or resist the leakage of gas from gas delivery pathway 28. As discussed above regarding seal ring 368, top housing may be formed from a material having a coefficient of friction that may provide a desired level of friction against ball 276, in order to allow ball 276 to rotate with a desired level of freedom or resistance.

Ball joint 50 may be configured to provide flexibility between separate components of gas delivery pathway 28. For example, hollow cylinder portion 360 of ball body 278 may be configured to be coupled to a first portion of gas delivery pathway 28 (such as a first gas deliver conduit 62, as shown in the embodiment of FIGS. 3A-3B), and a hollow cylinder portion 386 of bottom housing 270 may be configured to be coupled to a second portion of gas delivery pathway 28 (such as a second gas deliver conduit 64, as shown in the embodiment of FIGS. 3A-3B). Such portions of gas delivery pathway 28 (e.g., gas deliver conduits 62 and 64) may be coupled to hollow cylinder portions 360 and 386 in any suitable manner. For example, the portions of gas delivery pathway 28 may slide over or within hollow cylinder portions 360 and 386, respectively, in order to form a relatively secure connection between such components. As shown in FIG. 7B, ball 276 may rotate in any number of directions relative to housing 270, 274 in order to provide flexibility between separate components of gas delivery pathway 28 (e.g., gas deliver conduits 62 and 64).

In addition, as shown in FIG. 7B, hollow cylinder portion 360 may have a continuous cylindrical inner surface, and the seam or joint between ball body 278 and ball cop 280 may be located external to the gas flow passageway. Thus, there are no seams or joints between the components of ball 276 in the gas flow passageway, which may further reduce the leakage of gas from gas delivery pathway 28. Such configuration, as well as the multiple seals provided between ball 276 and adjacent components of ball joint 50, may prevent or resist gas from leaking or escaping, which may provide various advantages, such as reducing gas pressure losses and/or reducing or eliminating noise caused by gas escaping from the assembly, for example.

Figure 8A:
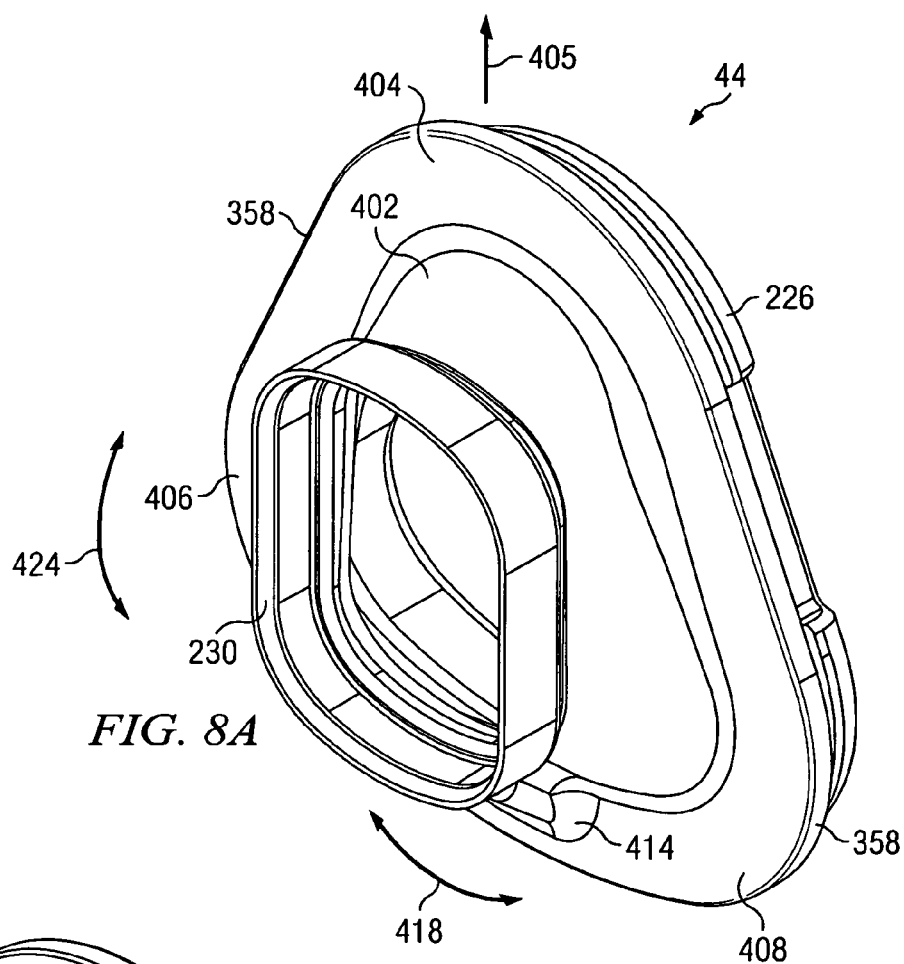
FIGS. 8A-8D illustrate an example configuration of a gasket, according to one embodiment of the disclosure.
Figure 8B:
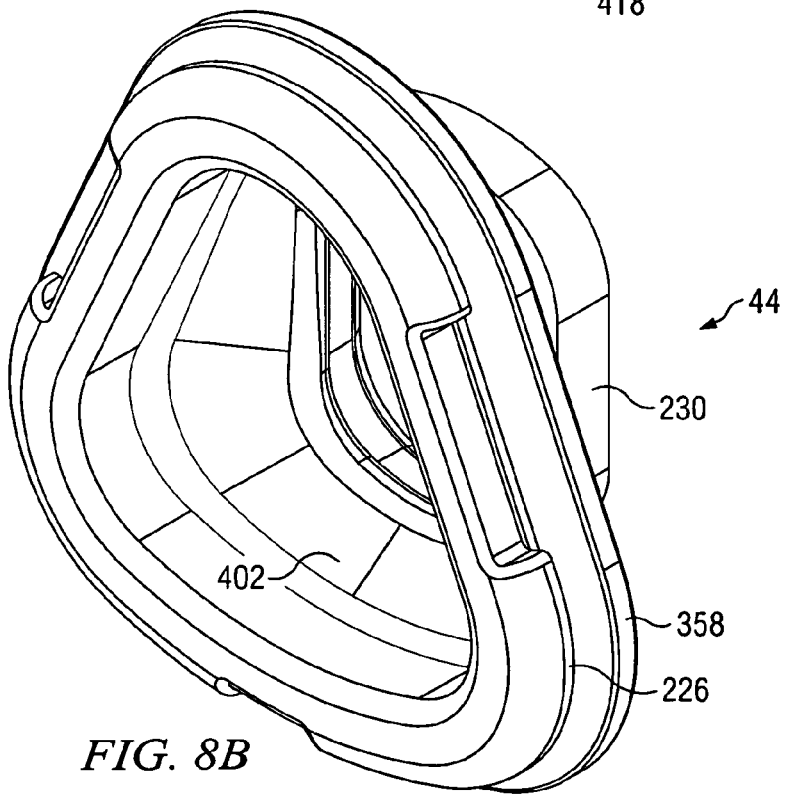
Figure 8C:
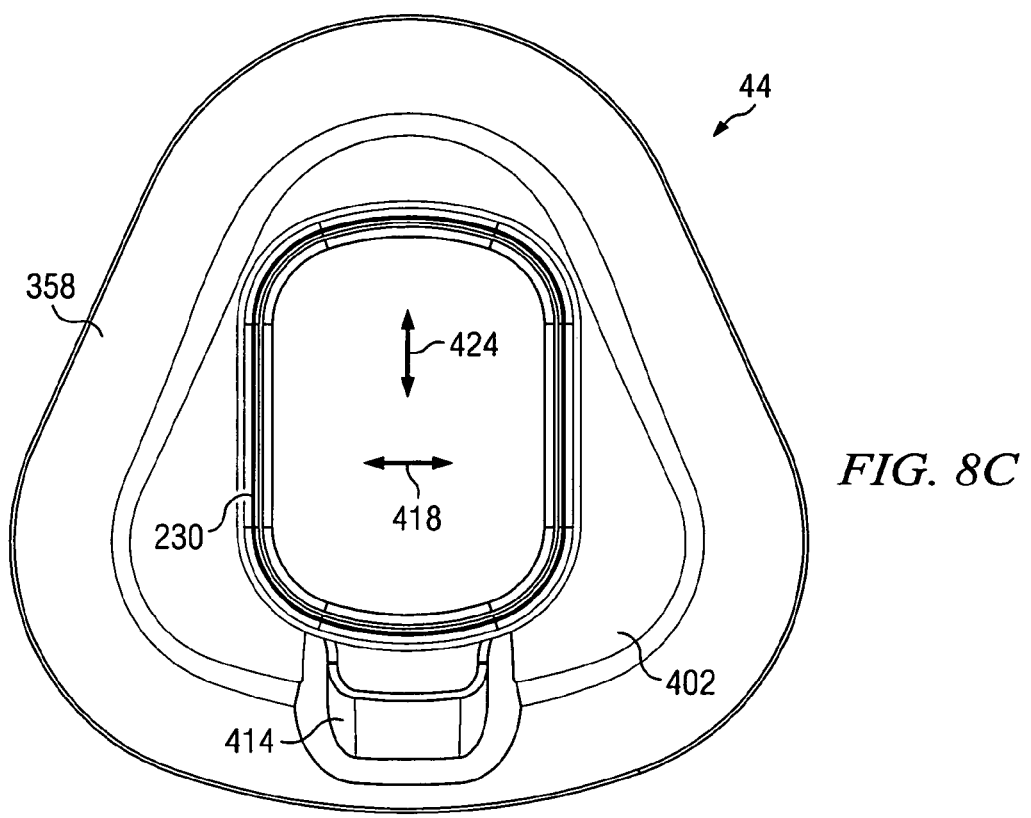
Figure 8D:
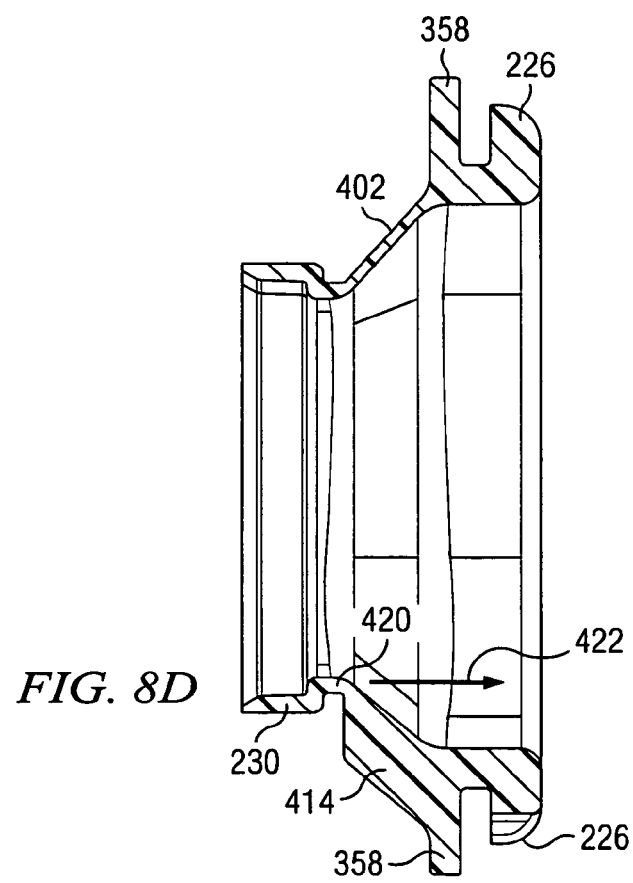

FIGS. 8A-8D illustrate an example configuration of a gasket 44, according to one embodiment of the disclosure. In particular, FIG. 8A is a three-dimensional view taken generally from the front of gasket 44, FIG. 8B is a three-dimensional view taken generally from the rear of gasket 44, FIG. 8C is a front view of gasket 44, and FIG. 8D is a cross-sectional view of gasket 44 taken along lines A-A shown in FIG. 8C.

In this embodiment, gasket 44 may include a first lip 226, a base flange 358, a skirt 402, and a second lip 230. Skirt 402 may generally couple base flange 358 with second lip 230. Base flange 358 may be configured to interface with a front surface 359 of base portion 68 of face mask 14 proximate an opening 228 formed in base portion 68 (see, e.g., FIG. 6). Base flange 358 may have any suitable shape. For example, base flange 358 may be shaped to correspond with the shape of opening 228 formed in base portion 68. In this particular embodiment, base flange 358 has a generally triangular shape with rounded corners. A first index 404 of the generally triangular shape generally points in a longitudinal direction 405 (i.e., pointing upward when the subject's head is in an upright position), while the other two indexes 406 and 408 of the generally triangular shape generally point downwardly and laterally.

First lip 226 may be formed proximate base flange 358 and may be configured to attach gasket 44 to base portion 68 of face mask 14. For example, first lip 226 may be malleably inserted into opening 228 formed in base portion 68 such that first lip 226 grips an inner ridge of base portion 68 proximate opening 228. First lip 226 may have any suitable shape and/or configuration for attaching gasket 44 to base portion 68. However, in other embodiments, gasket 44 may be otherwise coupled to base portion 68, such as using an adhesive, clips, taps, or one or more fasteners, for example.

Second lip 230 may be configured for coupling gasket 44 to a mask arm or arm assembly 16, such as discussed above regarding the embodiment shown in FIG. 6, for example. In some embodiments, second lip 230 may be configured to be wedged or otherwise held between two or more components of a mask arm assembly 16. In other embodiments, second lip 230 may be configured to grip a surface of a component of mask arm assembly 16, such as in the manner described above with respect to first lip 226 gripping an inner ridge of opening 228 in base portion 68, for example. However, in other embodiments, gasket 44 may be otherwise coupled to a mask arm assembly 16, such as using an adhesive, clips, taps, or one or more fasteners, for example.

Second lip 230 may have any suitable shape and/or configuration for attaching gasket 44 to a mask arm or arm assembly 16. In this embodiment, second lip 230 has a generally rectangular shape with rounded corners. Skirt 402 may be configured to couple first lip 226 and second lip 230. In this embodiment, skirt 402 transitions between the generally triangular base flange 358 and the generally rectangular second lip 230. In some embodiments, such as shown in FIGS. 8A-8D, skirt 402 comprises a generally direct and smooth transition between base flange 358 and second lip 230, which transition may be free of bellows and/or folds. In other embodiments, skirt 402 may include one or more bellows and/or folds.

Skirt 402 may be flexible to allow face mask 14 to flex in one or more directions relative to arm assembly 16. In some embodiments, skirt 402 may be flexible, but sufficiently rigid to substantially hold face mask 14 in constant position relative to arm apparatus 16 when face mask 14 is free from external (e.g., subject-induced) forces. Thus, gasket 44 may be formed from one or more materials suitable to provide such rigidity. For example, in certain embodiments, gasket 44 may be formed from a material having a durometer hardness of greater than 45 shore A, such as a suitable rubber, silicone, or polymer material. In particular embodiments, gasket 44 may be formed from a material having a durometer hardness of approximately 60 shore A, such as a suitable rubber, silicone, or polymer material. In a particular embodiment, gasket 44 may be formed from a silicone having a durometer hardness of approximately 60±5 shore A.

In certain embodiments, gasket 44 may include one or more portions or reinforcing members configured to control the flexibility of gasket 44 and/or to prevent or resist skirt 402 from collapsing or otherwise becoming undesirably deformed during use. In the embodiment shown in FIGS. 8A-8D, gasket 44 includes a reinforcing member 414 configured to prevent or resist skirt 402 from collapsing and/or to control the flexibility of face mask 14 relative to arm assembly 16 in the direction indicated by arrow 418 in FIG. 8A (or in other words, to restrict the movement of a lower edge 420 of second lip 230 relative to base flange 358 in the direction indicated by arrow 422 in FIG. 8D). Reinforcing member 414 may be distinct from or integrally formed with gasket 44. In this particular embodiment, reinforcing member 414 comprises a portion of skirt 402 formed with a greater thickness than other portions of skirt 402. For example, skirt 402 may have a substantially uniform thickness extending around the perimeter of skirt 402 excluding reinforcing member 414, and reinforcing member 414 has a substantially greater thickness than the remainder of skirt 402. In some embodiments, the thickness of reinforcing member 414 may be approximately two to ten times as great as the thickness of remaining portions of skirt 402. In a particular embodiment, the thickness of reinforcing member 414 may be approximately five times as great as the thickness of remaining portions of skirt 402.

In some embodiments, reinforcing member 414 may control the flexibility of face mask 14 relative to arm assembly 16 in the longitudinal direction indicated by arrow 418 in FIG. 8B, such that face mask 14 may be more easily rotated relative to arm apparatus 14 in a lateral direction indicated by arrow 424 in FIGS. 8A-8B than in the longitudinal direction indicated by arrow 418. Such control of flexibility in the longitudinal direction may reduce the likelihood of face mask 14 becoming disoriented from the subject's face, which may advantageously reduce the likelihood of gas leakage between face mask 14 and the subject's face.

FIG. 9 illustrates an example configuration of a mask body 12, according to one embodiment of the disclosure. In this embodiment, mask body 12 may include a pair of sidewalls 244 extending generally perpendicular from a generally flat portion. A pivot hole 242 and a notch 264 may be formed in each sidewall 244. Holes 248 may be configured for receiving lever pegs 240 and/or arm pegs 250 such that holes 248 define pivot points 76 about with lever 96 and/or arm member 72 may rotate. Notch 264 may be configured for receiving and/or guiding intermediate member pegs 262 as intermediate member 78 slides relative to mask body 12.

Mask body 12 may also include one or more strap guides 94 configured to guide and/or retain head strap 20. For example, in some embodiments in which head strap 20 includes a cord portion 92, strap guides 94 configured to guide and/or retain a cord portion 92. In addition, as shown in FIG. 9, strap guides 94 may be configured such that head strap 20 (e.g., cord portion 92) may be removed from strap guides 94 by manipulating head strap 20 (e.g., cord portion 92).

Mask body 12 may also include one or more notches 284 for receiving and/or securing ball joint 50 to mask body 12. For example, notches 284 may receive one or more tabs 282 coupled to a component of ball joint 50, such that ball joint 50 may be secured against mask body 12. In other embodiments, mask body 12 may include any other suitable notches or elements suitable to secure ball joint 50 to mask body 12.

Mask body 12 may also include an eyelet 106 through which a portion 104 of a head strap 20 may be routed to help secure mask body 12 against a subject's head.

Mask body 12 may be formed from any suitable material. In some embodiments, mask body 12 may be formed from a suitable plastic or polymer. In a particular embodiment, mask body 12 may be formed from a relatively rigid polycarbonate.

FIG. 10 illustrates an example configuration of a base pad 60, according to one embodiment of the disclosure. Base pad 60 may be configured to provide padding or cushioning between mask body 12 and a subject's head. Base pad 60 may have any suitable shape, which may correspond with a shape of mask body 12. Base pad 60 may be coupled to mask body 12 in any suitable manner. For example, in certain embodiments, base pad 60 may be coupled to a hook and loop fastener sheet 450 (see FIG. 11) secured to mask body 12.

Base pad 60 may be formed from any suitable material. In some embodiments, base pad 60 may be formed from a suitable flexible or cushioning material. In particular embodiments, base pad 60 may be formed from neoprene or breathoprene.

FIG. 11 illustrates an example configuration of a hook and loop fastener sheet 450, according to one embodiment of the disclosure. Sheet 450 may be configured for attaching base pad 60 to mask body 12 in any suitable manner. Sheet 450 may include one or more components. In this example, sheet 450 includes a pair of symmetrical halves. In some embodiments, one side of sheet 450 may be coupled to mask body 12 by adhesive, and the opposite side of sheet 450 may include hook and loop fasteners (e.g., Velcro™) to which base pad 60 may attach.

Figure 12:
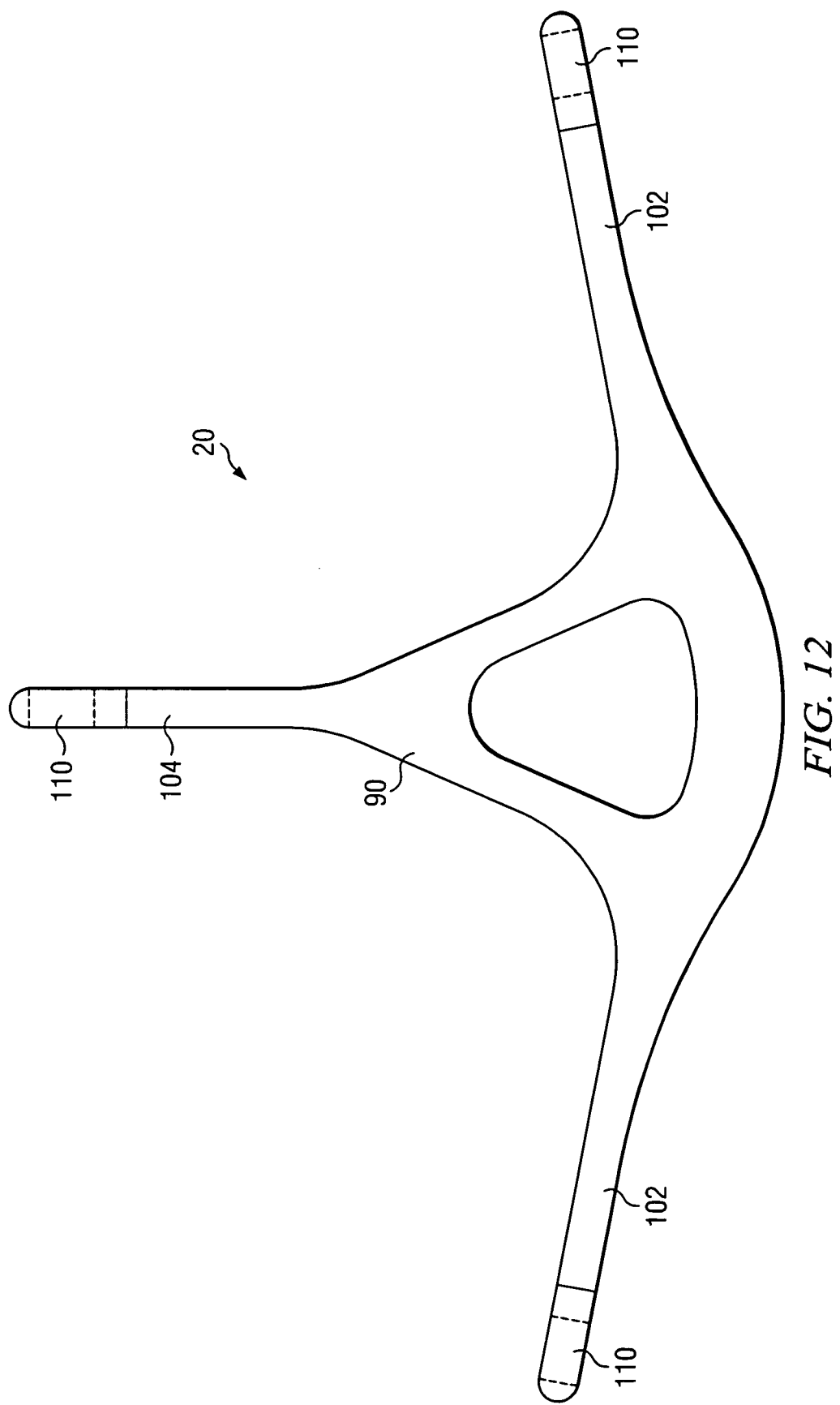
FIG. 12 illustrates an example configuration of a strap portion of a head strap, according to one embodiment of the disclosure.

FIG. 12 illustrates an example configuration of a strap portion 90 of a head strap 20, according to one embodiment of the disclosure. Strap portion 90 may be generally configured to secure mask assembly 10 onto a subject's head. In some embodiments, strap portion 90 may be configured to cooperate with one or more other components of head strap 20, such as a cord portion 92, in order to secure mask assembly 10 onto the subject's head. In the embodiment shown in FIG. 12, strap portion 90 may include a pair of elongated side portions 102 and an elongated top portion 104. Each elongated portion 102, 104 may include a hook and loop fasteners (e.g., Velcro™) portion 110 and may be routed through eyelets (e.g., eyelets 100 and 106) in order to secure mask body 12 against the subjects head, such as discussed above regarding the embodiment shown in FIGS. 3A-3B, for example.

Strap portion 90 may be formed from any suitable material. In some embodiments, strap portion 90 may be formed from a suitable flexible or cushioning material. In other embodiments, strap portion 90 may be formed from a generally non-flexible material. In particular embodiments, strap portion 90 may be formed from neoprene or breathoprene.

Figures 13A, 13B:
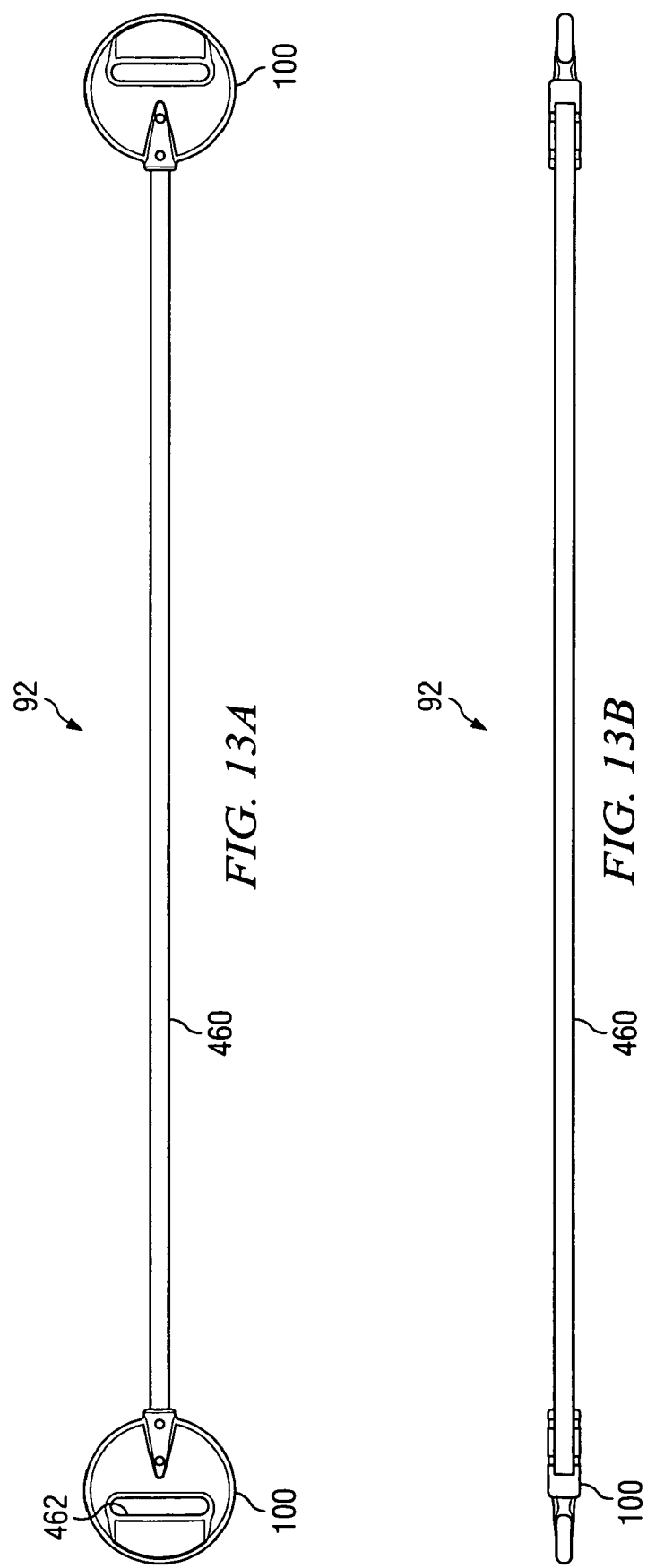
FIG. 13 illustrates an example configuration of a cord portion of a head strap, according to one embodiment of the disclosure.

FIGS. 13A and 13B illustrate an example configuration of a cord portion 92 of a head strap 20, according to one embodiment of the disclosure. Cord portion 92 may be generally configured to secure mask assembly 10 onto a subject's head. In some embodiments, cord portion 92 may be configured to cooperate with one or more other components of head strap 20, such as a strap portion 92, in order to secure mask assembly 10 onto the subject's head. In the embodiment shown in FIG. 13, cord portion 92 may include a cord 460 and an eyelet 100 attached at each end of cord 460. Cord 460 may be formed from any suitable material. In some embodiments, cord 460 may be formed from a flexible material, such as elastic, for example. In other embodiments, cord 460 may be formed from a generally non-flexible material.

Eyelets 100 may be formed from any suitable material, such as a plastic or polymer, for example, and may be coupled to cord 460 in any suitable manner, such as by insert molding, for example. Each eyelets 100 may include an opening 462 through which elongated side portions 102 of strap portion 90 may be routed, such as described herein.

Figure 14:
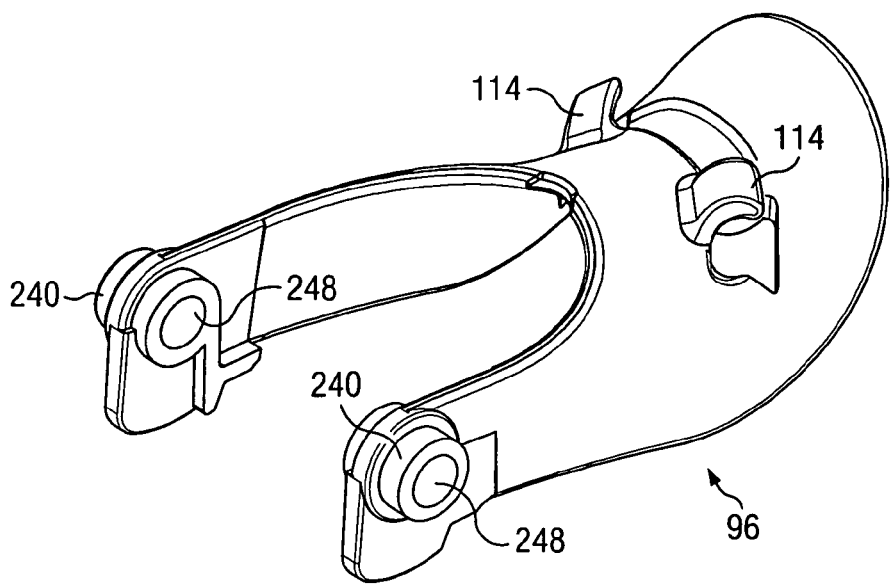
FIG. 14 illustrates an example configuration of a lever, according to one embodiment of the disclosure.

FIG. 14 illustrates an example configuration of a lever 96, according to one embodiment of the disclosure. Lever 96 may be generally configured for adjusting head strap 20 around a subject's head, such as to tighten or loosen head strap 20 around the subject's head, for example. For example, lever 96 may operate as a cinch clamp to control the tightness of head strap 20 around the subject's head. In this embodiment, lever 96 may include a pair of lever pegs 240 that may be inserted into pivot holes 242 formed in mask body 12 such that lever 96 may rotate about lever pegs 240 relative to mask body 12. A hole 248 may be formed in each lever peg 240 and configured to receive an arm peg 250 formed on arm member 72, such that arm member 72 may rotate about the same pivot points as lever 96. Lever 96 may also include one or more strap retention members 114 that may be configured to hold or retain cord portion 92 of head strap 20.

Lever 96 may be formed from any suitable material. In some embodiments, lever 96 may be formed from a suitable plastic or polymer. In a particular embodiment, lever 96 may be formed from a relatively rigid polycarbonate.

FIGS. 15A and 15B illustrate an example configuration of an arm member 72, according to one embodiment of the disclosure. In particular, FIG. 8A is a three-dimensional view of arm member 72, and FIG. 15B is a side view of arm member 72. Arm member 72 may be generally configured for supporting face mask 14.

In this embodiment, arm member 72 may include a pair of arm pegs 250 that may be inserted into holes 248 formed in lever pegs 240, which may be inserted into pivot holes 242 formed in mask body 12, such that arm member 72 may rotate relative to mask body 12. Alternatively, arm pegs 250 may be inserted directly into pivot holes 242 formed in mask body 12 such that arm member 72 may rotate relative to mask body 12.

In addition, one or more threads 258 may be formed on an outer surface of arm member 72 which may be configured to interact with threaded portion 82 of intermediate member 78 in order to rotate arm member 72 as desired. In this embodiment, threads 258 may comprise ribs extending a relatively short distance around an outer surface of arm member 72. A series of threads 258 may be formed on opposing sides of arm member 72. In addition, in this embodiment, a notch 304 may extend across and through each series of threads 258. Each notch 304 may be configured to guide a guide member 306 formed on an interior surface of body portion 80 of intermediate member 78 along arm member 72.

Arm member 72 may also include one or more notches 470 configured to receive one or more elbow pegs 472 formed in elbow 66 such that elbow 66 may be removably coupled to arm member 72. For example, in this embodiment, notches 470 are configured such that elbow pegs 472 may be inserted upward into notches 470 and elbow 66 may then be rotated in order to secure elbow pegs 472 with notches 470.

Arm member 72 may be formed from any suitable material. In some embodiments, arm member 72 may be formed from a suitable plastic or polymer. In a particular embodiment, arm member 72 may be formed from a relatively rigid polycarbonate.

FIG. 16 illustrates an example configuration of a body portion 80 of an intermediate member 78, according to one embodiment of the disclosure. Body portion 80 may be generally configured to cooperate with threaded portion 82, arm member 72, and mask body 12 in order to adjust the positioning of arm member 72.

In this embodiment, body portion 80 may be generally U-shaped. In addition, body portion 80 may include a ring-shaped portion 480 configured to be coupled (e.g., rotatably) to threaded portion 82 in any suitable manner. For example, body portion 80 may include one or more tabs 482 extending from an inner perimeter of ring-shaped portion 480. Tabs 482 may be configured to slide within a groove 490 extending around an outer perimeter of threaded portion 82 such that threaded portion 82 may be coupled (e.g., rotatably) to body portion 80. Body portion 80 may also include a pair of intermediate member pegs 262 configured to be inserted into and/or guided by notches 264 formed in sidewalls 244 of mask body 12.

Body portion 80 may be formed from any suitable material. In some embodiments, body portion 80 may be formed from a suitable plastic or polymer. In a particular embodiment, body portion 80 may be formed from a relatively rigid polycarbonate.

Figure 17:
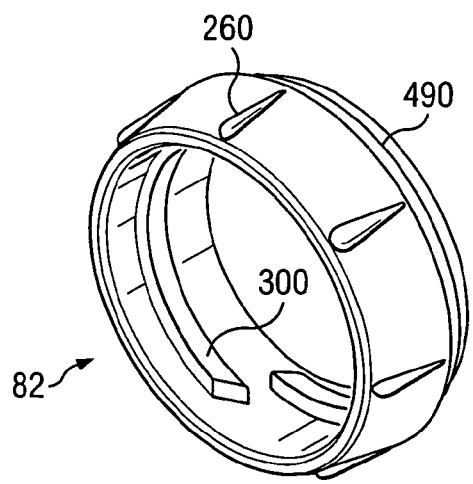
FIG. 17 illustrates an example configuration of a threaded portion of an intermediate member, according to one embodiment of the disclosure.

FIG. 17 illustrates an example configuration of a threaded portion 82 of an intermediate member 78, according to one embodiment of the disclosure. Threaded portion 82 may be generally configured to cooperate with body portion 80, arm member 72, and mask body 12 in order to adjust the positioning of arm member 72. Threaded portion 82 may be ring-shaped and may include one or more threads 300 formed on an inner surface of the ring. Threads may interact with one or more series of threads 258 formed on an outer surface of arm member 72.

Threaded portion 82 may also include a groove 490 extending around an outer perimeter of threaded portion 82. Groove 490 may be configured to receive one or more tabs 482 of body portion 80 such that threaded portion 82 may be coupled (e.g., rotatably) to body portion 80. Threaded portion 82 may also include grips 260 on an outer surface that may provide the subject a better grip for rotating threaded portion 82 in order to pivot arm assembly 16.

Body portion 80 may be formed from any suitable material. In some embodiments, body portion 80 may be formed from a suitable plastic or polymer. In addition, body portion 80 may be formed from a material having a particular (e.g., relatively low) coefficient of friction in order to provide a desired (e.g., relatively low) amount of friction between threads 300 and threads 258 on arm member 72. For example, in particular embodiments, body portion 80 may be formed from a polybutylene terephthalate (PBT) polymer, for example.

Figure 18A:
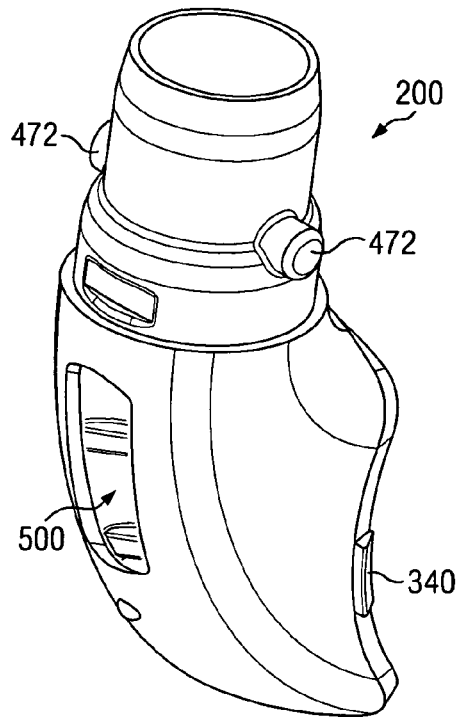
FIGS. 18A-18B illustrate an example configuration of a front elbow portion, according to one embodiment of the disclosure.
Figure 18B:
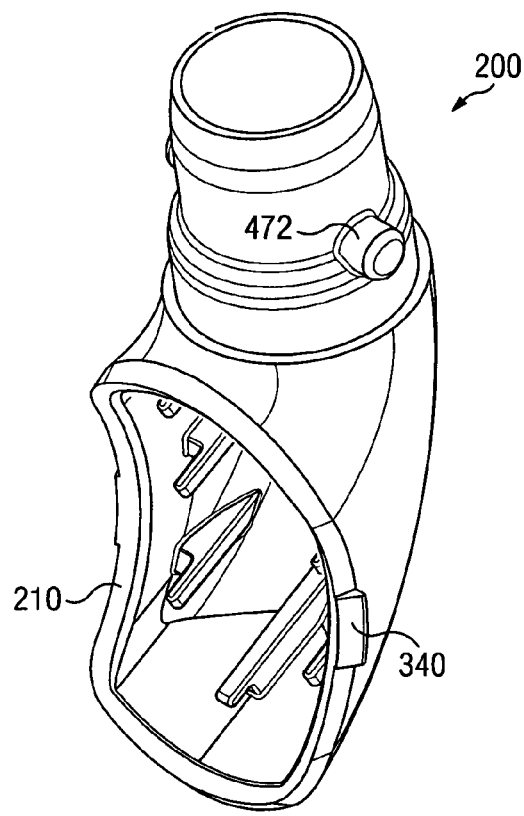

FIGS. 18A and 18B illustrate an example configuration of a front elbow portion 200, according to one embodiment of the disclosure. In particular, FIG. 18A is a three-dimensional view taken from the front of front elbow portion 200, and FIG. 18B is a three-dimensional view taken from the rear of front elbow portion 200. Front elbow portion 200 may be generally configured for facilitating the coupling of face mask 14 to arm member 72. In addition, front elbow portion 200 may be generally configured to interact with rear elbow portion 204 to form a pivot joint 86 allowing face mask 14 to rotate in a generally longitudinal direction.

Front elbow portion 200 may include one or more elbow pegs 472 configured to be received into one or more notches 470 formed in arm member 72 in order to removably couple front elbow portion 200 to arm member 72. For example, in this embodiment, elbow pegs 472 may be inserted upward into notches 470 and front elbow portion 200 may then be rotated in order to secure elbow pegs 472 with notches 470.

Front elbow portion 200 may include tabs 340 configured to be inserted into curved notches 342 formed in rear elbow portion 204, such that rear elbow portion 204 may slide through an arc relative to front elbow portion 200 in order to rotate face mask 14 in a generally longitudinal direction. In addition, a rear surface 210 of front elbow portion 200 may have a curved shape configured to cooperate with a curved front surface of rear elbow portion 204 as rear elbow portion 204 slides through an arc relative to front elbow portion 200. Front elbow portion 200 may also be configured to receive a slider seal 202 that may provide an interface between front elbow portion 200 and rear elbow portion 204 as elbow portion 204 slides relative to front elbow portion 200. Slider seal 202 may generally be operable to reduce the amount of friction between front elbow portion 200 and rear elbow portion 204.

Front elbow portion 200 may also include an opening 500 configured to receive an exhaust member 52 allowing gas to escape from elbow 66 to the surrounding environment. Front elbow portion 200 may be formed from any suitable material. In some embodiments, front elbow portion 200 may be formed from a suitable plastic or polymer. In a particular embodiment, front elbow portion 200 may be formed from a relatively rigid polycarbonate.

Figure 19A:
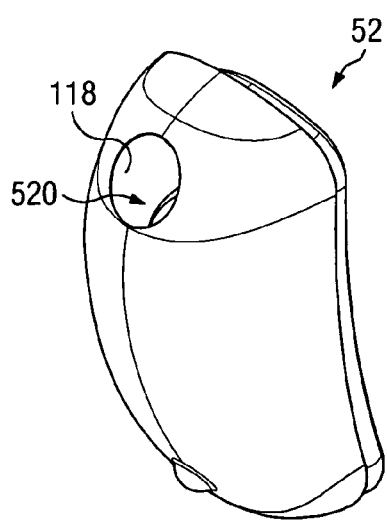
FIGS. 19A-19B illustrate an example configuration of an exhaust port, according to one embodiment of the disclosure.
Figure 19B:
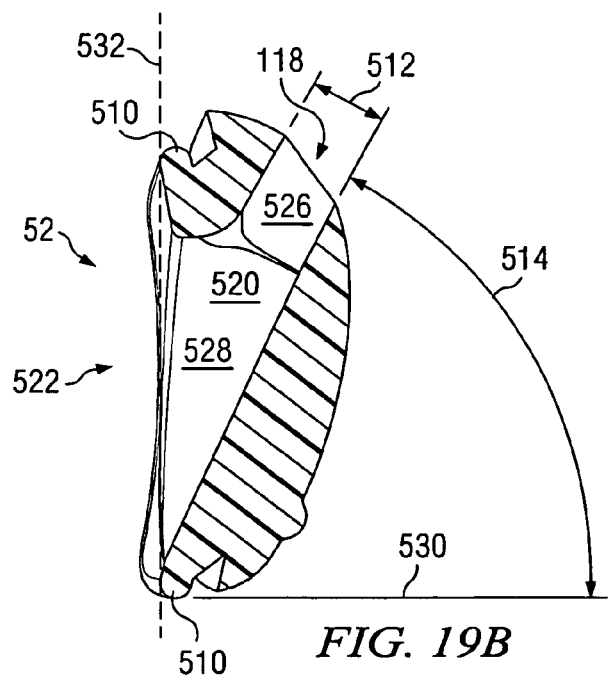

FIGS. 19A and 19B illustrate an example configuration of an exhaust member 52, according to one embodiment of the disclosure. In particular, FIG. 19A is a three-dimensional view of exhaust member 52, and FIG. 19B is a cross-sectional side view of exhaust member 52. Exhaust member 52 may generally be configured to allow gas exhaled by the subject (e.g., $CO_2$) to escape from mask apparatus 10 to the surrounding environment. Exhaust member 52 may be integrated with, or coupled to, elbow 66 of arm assembly 16 in any suitable manner. For example, exhaust member 52 may include a flexible lip 510 configured to be inserted into opening 500 in front elbow portion 200 to secure exhaust member 52 to front elbow portion 200.

Exhaust member 52 may include one or more gas passageways 520 configured to allow gas (e.g., exhaust gas exhaled by a subject) to flow out from mask assembly 10 and into the surrounding environment. For example, in some embodiments, a gas exhaust pathway may allow gas to flow from the subject, through face mask 14, through gasket 44, through elbow 66, through one or more gas passageways 520, and into the surrounding environment. In particular embodiments, such as the embodiment shown in FIGS. 19A-19B, mask apparatus 10 may include a single gas passageway 520. In other embodiments, mask apparatus 10 may include multiple gas passageways 520.

As shown in FIG. 19B, the single gas passageway 520 may extend from a first opening 118 formed in a first side of exhaust member 52 to a second opening 522 formed in a second side of exhaust member 52. In some embodiments, the size and/or shape of gas passageway 520 may be configured to (a) allow a desired amount of gas flow through gas passageway 520 and/or (b) to reduce or minimize the amount of noise created by gas flowing through gas passageway 520.

For example, a diameter 512 and/or a cross-sectional area $A_{118}$ of first opening 118 may be appropriately sized to allow a desired amount of gas flow through gas passageway 520 and/or to reduce or minimize the amount of noise created by gas flowing through gas passageway 520. In some embodiments, diameter 512 may be about 0.10 inches to about 0.20 inches, and cross-sectional area $A_{118}$ may be about 0.008 square inches to about 0.031 square inches. In particular embodiments, diameter 512 may be about 0.125 inches to about 0.175 inches, and cross-sectional area $A_{118}$ may be about 0.012 square inches to about 0.024 square inches. In one embodiment, diameter 512 may be about 0.146 inches, and cross-sectional area $A_{118}$ may be about 0.017 square inches.

In addition, in some embodiments, a cross-sectional area $A_{522}$ of second opening 522 may have a different shape and/or size than cross-sectional area $A_{118}$ of first opening 118. For example, cross-sectional area $A_{522}$ of second opening 522 may be substantially greater than a cross-sectional area $A_{118}$ of first opening 118. In certain embodiments, cross-sectional area $A_{522}$ may be at least twice as great as cross-sectional area $A_{118}$. In one particular embodiment, cross-sectional area $A_{522}$ may be more than three times as great as cross-sectional area $A_{118}$. In addition, in some embodiments, cross-sectional area $A_{118}$ may have a substantially circular shape and cross-sectional area $A_{522}$ may have a substantially elongated, or oval, shape.

In some embodiments, e.g., the embodiment shown in FIGS. 19A-19B, gas passageway 520 may include a substantially cylindrical portion 526 and a transition portion 528 that may transition between the cross-section of cylindrical portion 526 and the cross-section of second opening 522. In some embodiments, a length (or depth) of cylindrical portion 526 may be appropriately sized to reduce or minimize the amount of noise created by gas flowing through gas passageway 520.

In addition, in some embodiments, gas passageway 520 or a portion of gas passageway 520 (e.g., cylindrical portion 526) may be oriented at a particular angle 514 relative to a generally horizontal axis 530 to provide one or more desired performance characteristics. For example, angle 514 may be selected to reduce or minimize the flow of exhaust gas incident upon another person, such as the subject's bed partner and/or to reduce or minimize the amount of noise created by gas flowing through gas passageway 520. For example, angle 514 may be greater than 35 degrees. In some embodiments, angle 514 may be about 50 degrees to about 80 degrees. In a particular embodiment, angle 514 may be 65±5 degrees. Generally horizontal axis 530 be defined as an axis perpendicular to a generally vertical axis 532 defined by the rear edges of member 52 (e.g., lip 510).

Exhaust member 52 may be formed from any suitable material. Exhaust member 52 may be formed from a flexible material, such as a rubber, silicone or polymer, for example. In some embodiments, exhaust member 52 may be formed from a material having a durometer hardness of approximately 45±10 shore A. In particular embodiments, exhaust member 52 may be formed from a thermoplastic elastomer, such as Santoprene™ 281-45MED, for example.

Figure 20:
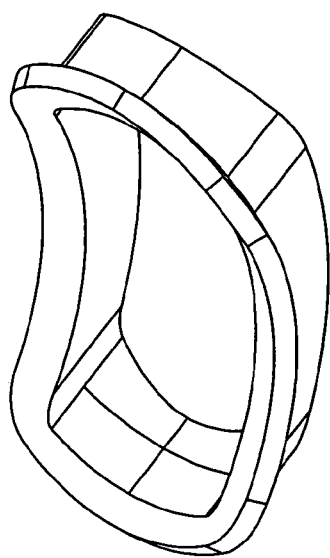
FIG. 20 illustrates an example configuration of a slider seal, according to one embodiment of the disclosure.

FIG. 20 illustrates an example configuration of a slider seal 202, according to one embodiment of the disclosure. Slider seal 202 may generally be configured to provide an interface between front elbow portion 200 and rear elbow portion 204 to provide a desired (e.g., relatively low) level of friction between rear elbow portion 204 and front elbow portion 200 as rear elbow portion 204 slides relative to front elbow portion 200. Slider seal 202 may be received in an opening formed in front elbow portion 200.

Slider seal 202 may be formed from any suitable material. In some embodiments, slider seal 202 may be formed from a material having a relatively low coefficient of friction, such as a silicon or polymer material. In a particular embodiment, slider seal 202 may be formed from a silicone having a durometer hardness of approximately 60±5 shore A.

Figure 21A:
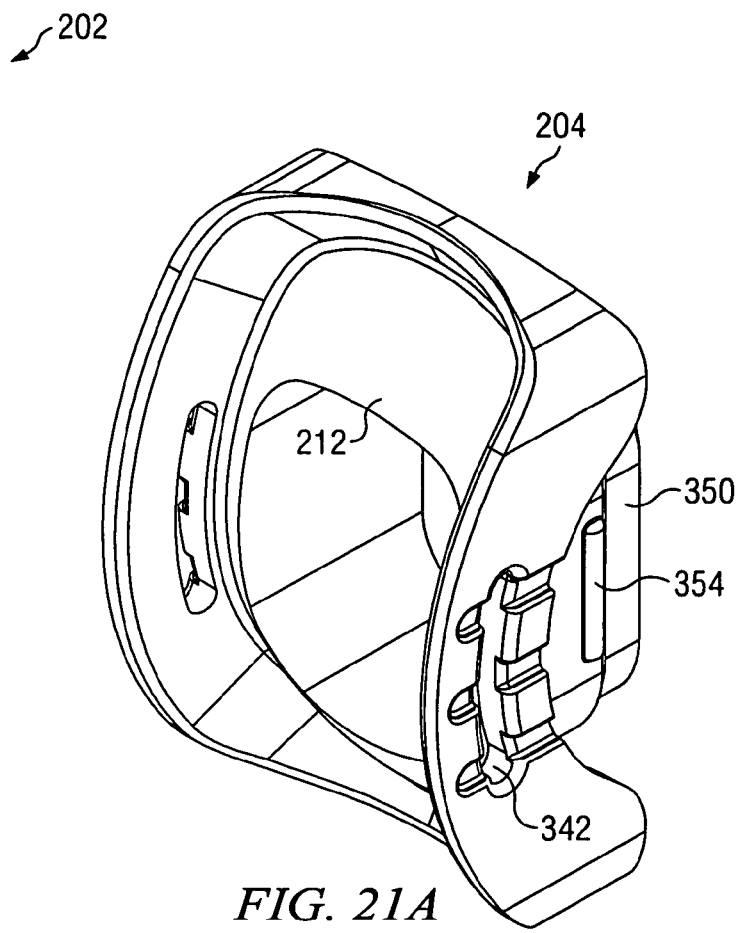
FIGS. 21A-21B illustrate an example configuration of a rear elbow portion, according to one embodiment of the disclosure.
Figure 21B:
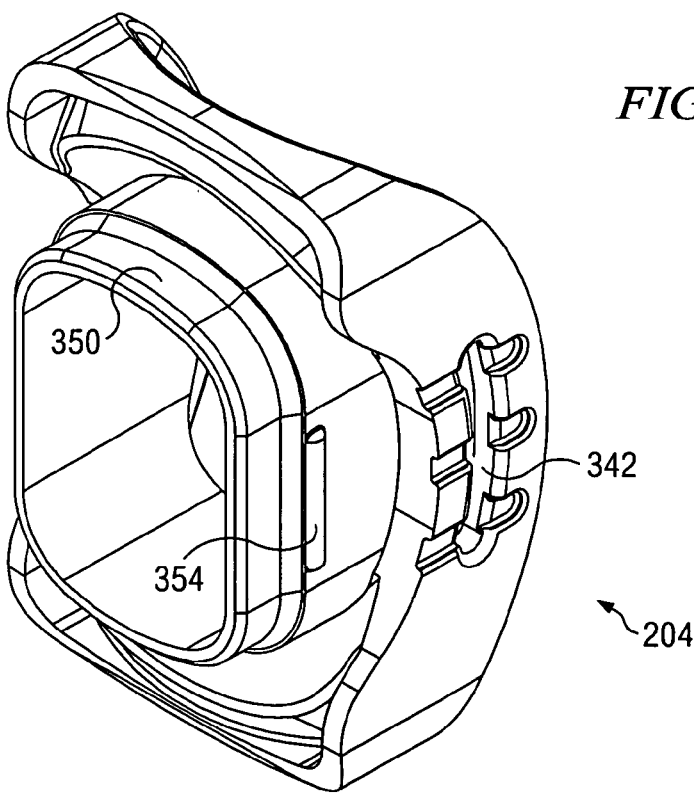

FIGS. 21A and 21B illustrate an example configuration of a rear elbow portion 204, according to one embodiment of the disclosure. In particular, FIG. 21A is a three-dimensional view taken from the front of rear elbow portion 204, and FIG. 21B is a three-dimensional view taken from the rear of rear elbow portion 204. Rear elbow portion 204 may be generally configured to interact with front elbow portion 200 to form a pivot joint 86 allowing face mask 14 to rotate in a generally longitudinal direction.

Rear elbow portion 204 may include notches 342 configured to receive tabs 340 formed on front elbow portion 200 in order to secure front elbow portion 200 to rear elbow portion 204. In some embodiments, notches 342 are curved such that rear elbow portion 204 may slide through an arc relative to front elbow portion 200 in order to rotate face mask 14 in a generally longitudinal direction. In addition, a front surface 212 of rear elbow portion 204 may have a curved shape configured to cooperate with a curved rear surface of front elbow portion 200 as rear elbow portion 204 slides through an arc relative to front elbow portion 200. Rear elbow portion 204 may also include tabs 354 configured to be inserted into notches 356 formed in clip 206, such that clip 206 may be secured to rear elbow portion 204.

Rear elbow portion 204 may be formed from any suitable material. In some embodiments, rear elbow portion 204 may be formed from a suitable plastic or polymer. In a particular embodiment, rear elbow portion 204 may be formed from a relatively rigid polycarbonate.

Figure 22:
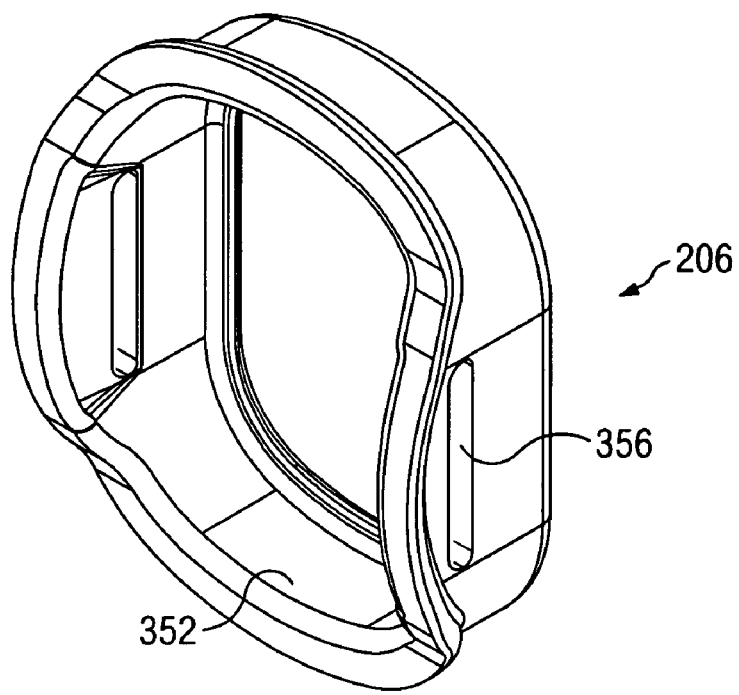
FIG. 22 illustrates an example configuration of a clip, according to one embodiment of the disclosure.

FIG. 22 illustrates an example configuration of a clip 206, according to one embodiment of the disclosure. Clip 206 may be generally configured to secure gasket 44 to elbow 66. For example, second lip 230 of gasket 44 may be held (e.g., wedged) between an internal surface 352 of clip 206 and an external surface 350 of rear elbow portion 204. Clip 206 may also include notches 356 into which tabs 354 formed on rear elbow portion 204 may be inserted in order to secure clip 206 to rear elbow portion 204.

Clip 206 may be formed from any suitable material. In some embodiments, clip 206 may be formed from a suitable plastic or polymer. In a particular embodiment, clip 206 may be formed from a relatively rigid polycarbonate.

Figure 23:
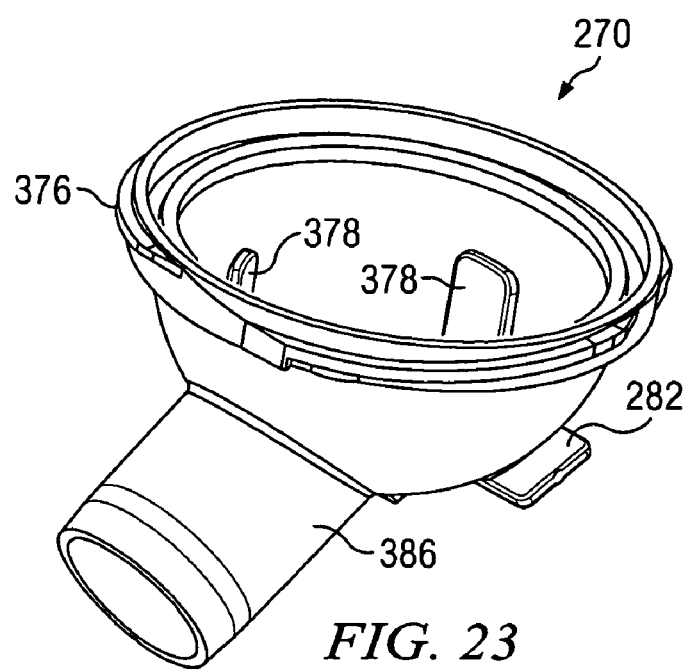
FIG. 23 illustrates an example configuration of a bottom housing of a ball joint, according to one embodiment of the disclosure.

FIG. 23 illustrates an example configuration of a bottom housing 270 of a ball joint 50, according to one embodiment of the disclosure. Bottom housing 270 may generally be configured to cooperate with a top housing 274 to provide a housing for a ball 276 of ball joint 50. Bottom housing 270 may include a cylindrical portion 386 configured to be coupled to a component of a gas delivery pathway 28, such as a length of flexible tubing, for example.

Bottom housing 270 may also include a thread or lip 376 that may interact with a thread or lip 375 of top housing 274 to screw or otherwise secure top housing 274 onto bottom housing 270. In addition, bottom housing 270 may include one or more stops 378 configured to limit the amount of flexing of a seal ring 368 disposed within bottom housing 270. In a particular embodiment, bottom housing 270 may include three stops 378 located around an inner perimeter of bottom housing 270. Bottom housing 270 may also include one or more tabs 282 that may slide into one or more notches 284 formed in mask body 12 in order to removably secure bottom housing 270 to mask body 12.

Bottom housing 270 may be formed from any suitable material. In some embodiments, bottom housing 270 may be formed from a suitable plastic or polymer. In a particular embodiment, bottom housing 270 may be formed from a relatively rigid polycarbonate.

FIGS. 24A and 24B illustrate an example configuration of a seal/spring 272, according to one embodiment of the disclosure. In particular, FIG. 24A is a three-dimensional exploded view of seal/spring 272, and FIG. 24B is a cross-sectional side view of seal/spring 272. Seal/spring 272 may be generally configured to provide a seal against ball 276 to prevent or resist gas from leaking out of ball joint 50.

Seal/spring 272 may include a flexible ring 366 integrated with, or coupled to, a seal ring 368 in any suitable manner. For example, in one embodiment, flexible ring 366 and seal ring 368 are molded together to form an integrated component. Flexible ring 366 may be configured to be received within, or coupled to, bottom housing 270 in any suitable manner such that seal ring 368 may be suspended from contacting bottom housing 270. Flexible ring 366 may include a lip 370 that may rest against an edge of bottom housing 270.

Seal ring 368 may be configured to receive ball 276 such that ball 276 may rotate relative to seal ring 368. Seal ring 368 may include a circular rim 371 that may provide a seal against the outer surface of ball 276. Seal ring 368 may be formed from a suitable material providing a desired level of friction between rim 371 and ball 276 in order to allow ball 276 to rotate with a desired level of freedom or resistance. In certain embodiments, flexible ring 366 may be formed from a flexible and/or resilient material, such as a rubber, silicone, or polymer, and seal ring 368 may be formed from a more rigid material having a lower coefficient of friction than flexible ring 366. In particular embodiments, flexible ring 366 may be formed from a silicone having a durometer hardness of approximately 60±5 shore A, and seal ring 368 may be formed from a polybutylene terephthalate (PBT) polymer, for example.

Figure 25A:
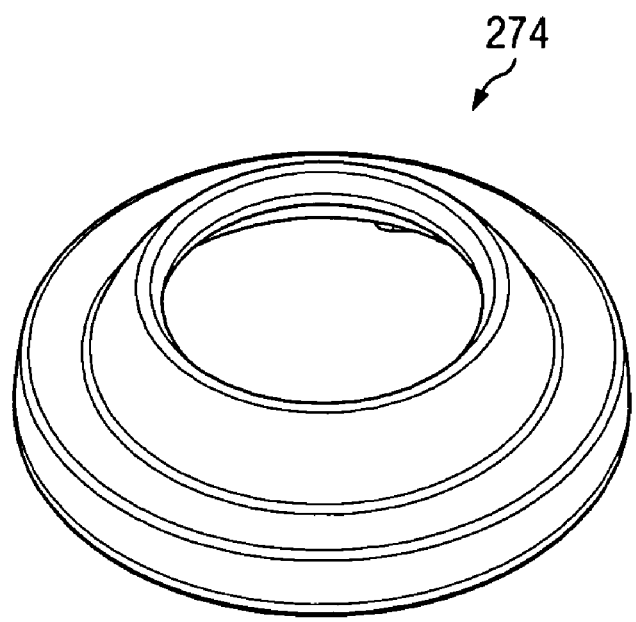
FIGS. 25A-25B illustrate an example configuration of a top housing of a ball joint, according to one embodiment of the disclosure.
Figure 25B:
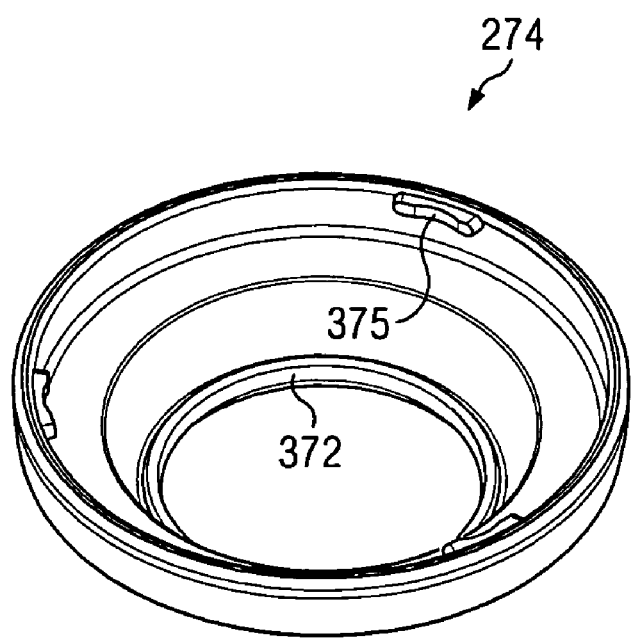

FIGS. 25A and 25B illustrate an example configuration of a top housing 274, according to one embodiment of the disclosure. In particular, FIG. 25A is a three-dimensional view taken from the top of top housing 274, and FIG. 25B is a three-dimensional view taken from the top of top housing 274. Top housing 274 may be generally configured to cooperate with a bottom housing 270 to provide a housing for a ball 276 of ball joint 50.

Top housing 274 may include one or more threads or lips 375 that may interact with a thread or lip 376 of bottom housing 270 to screw or otherwise secure top housing 274 onto bottom housing 270. Top housing 274 may include a circular rim 380 that may provide a seal against the outer surface of ball 276. Top housing 274 may be formed from a suitable material providing a desired level of friction between rim 380 and ball 276 in order to allow ball 276 to rotate with a desired level of freedom or resistance. In some embodiments, top housing 274 may be formed from a suitable plastic or polymer. In a particular embodiment, top housing 274 may be formed from a relatively rigid polycarbonate.

Figure 26A:
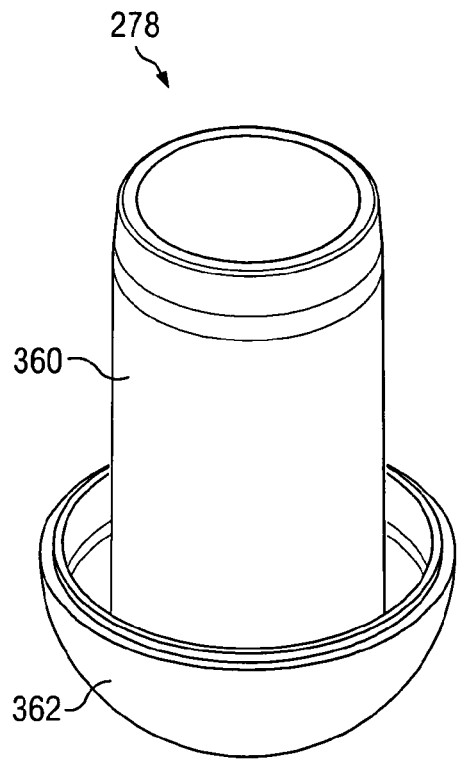
FIGS. 26A-26B illustrate an example configuration of a ball body, according to one embodiment of the disclosure.
Figure 26B:
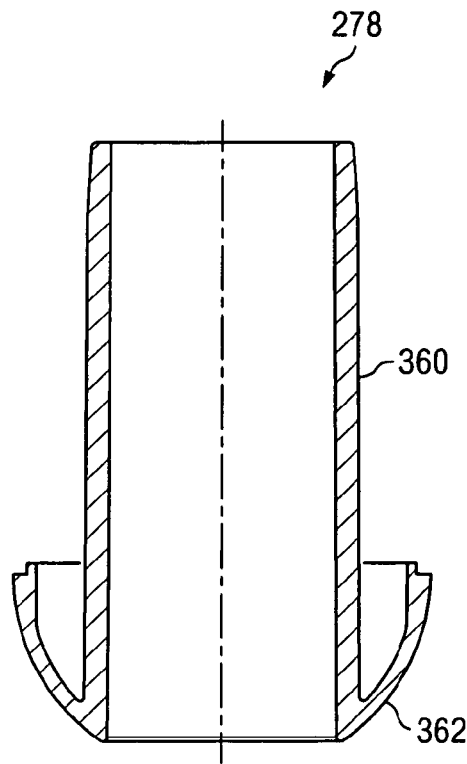
Figure 27A:
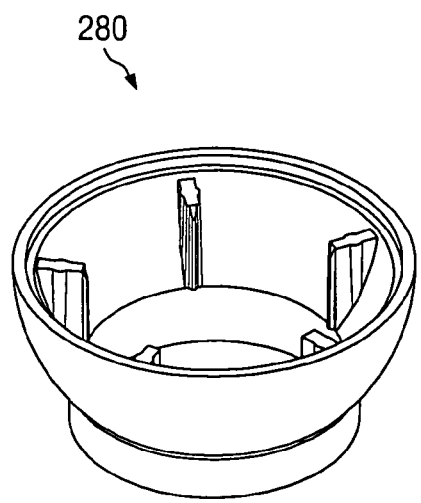
FIGS. 27A-27B illustrate an example configuration of a ball cap, according to one embodiment of the disclosure.
Figure 27B:
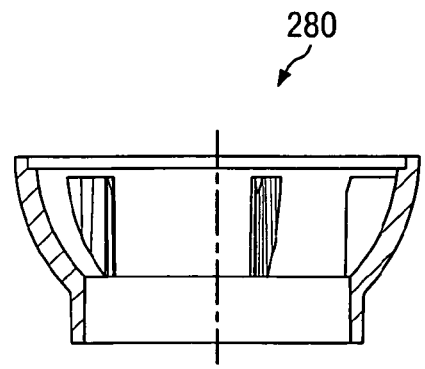

FIGS. 26A and 26B illustrate an example configuration of a ball body 278, according to one embodiment of the disclosure. In particular, FIG. 26A is a three-dimensional of ball body 278, and FIG. 26B is a cross-sectional side view of ball body 278. FIGS. 27A and 27B illustrate an example configuration of a ball cap 280, according to one embodiment of the disclosure. In particular, FIG. 27A is a three-dimensional of ball cap 280, and FIG. 27B is a cross-sectional side view of ball cap 280.

Ball body 278 and ball cap 280 may combine to form ball 276. Ball body 278 may include a hollow cylindrical portion 360 and a hemispherical portion 362 extending from a first end of hollow cylindrical portion 360. Ball body 278 and/or ball cap 280 may be formed from a material having a particular (e.g., relatively low) coefficient of friction in order to provide a desired (e.g., relatively low) amount of friction between ball 276 and seal ring 368 and/or between ball 276 and top housing 274. For example, in particular embodiments, Ball body 278 and/or ball cap 280 may be formed from a polybutylene terephthalate (PBT) polymer, for example.

Although the disclosed embodiments have been described in detail, it should be understood that various changes, substitutions and alterations can be made herein without departing from the spirit and scope of the disclosure as illustrated by the following claims. For example, it should be understood that in various embodiments, gas delivery mask apparatus 10 may include any combination of one, some or all of the various components and/or features discussed above and/or any one or more additional components and/or features.

What is claimed is:

1. An adjustable gas delivery system, comprising:
a face mask configured to deliver gas to a subject, the face mask including a flexible cushion portion configured to interface with the subject's face and a rigid base portion configured to support the cushion portion, the rigid base portion including a gas inlet;
an arm apparatus configured to deliver gas to the face mask, the arm apparatus including a gas outlet, the gas outlet of the arm apparatus having a cross-sectional area smaller than a cross-sectional area of the gas inlet of the base portion of the face mask; and
a gasket coupling the gas outlet of the arm apparatus with the gas inlet of the face mask, the gasket being flexible such that the orientation of the face mask relative to the arm apparatus is adjustable.

2. A system according to claim 1, wherein the gasket substantially holds the face mask in constant position relative to the arm apparatus when the face mask is not interfacing with the subject.

3. A system according to claim 1, wherein the gasket is formed from a material having a durometer hardness of greater than 45 shore A.

4. A system according to claim 1, wherein the gasket is formed from a material having a durometer hardness of approximately 60 shore A.

5. A system according to claim 1, wherein the cross-section of the gas outlet of the arm apparatus is substantially rectangular in shape and the cross-section of the gas inlet of the face mask is substantially triangular in shape.

6. A system according to claim 1, wherein the gasket is configured such that the face mask is more easily rotated relative to the arm apparatus in a first direction than in a second direction perpendicular to the first direction.

7. A system according to claim 1, wherein:
the arm apparatus extends generally in a longitudinal direction; and
the gasket is configured such that the face mask is more easily rotated relative to the arm apparatus in a lateral direction perpendicular to the longitudinal direction than in the longitudinal direction.

8. A system according to claim 1, wherein the gasket includes a reinforced portion that substantially prevents the gasket from collapsing.

9. A system according to claim 1, wherein:
the gasket includes a gasket skirt located generally between the face mask and the arm assembly, the gasket skirt having a substantially uniform thickness around a first portion of the gasket skirt; and
the reinforced portion of the gasket comprises a second portion of the gasket skirt having a thickness significantly greater than the substantially uniform thickness of the first portion of the gasket skirt.

10. A gas delivery mask apparatus, comprising:
a mask body base;
a mask head strap configured to secure the mask body to a subject's head;
a face mask configured to deliver gas to a subject, the face mask including a flexible cushion portion configured to interface with the subject's face and a rigid base portion configured to support the cushion portion, the rigid base portion including a gas inlet;
a mask arm coupled to the mask base and configured to support the face mask and deliver gas to the face mask, the mask arm including a gas outlet, the gas outlet of the mask arm having a cross-sectional area smaller than a cross-sectional area of the gas inlet of the base portion of the face mask; and
a mask gasket coupling the gas outlet of the mask arm with the gas inlet of the face mask, the mask gasket being flexible such that the orientation of the face mask relative to the mask arm is adjustable.

11. A mask apparatus according to claim 10, wherein the gasket substantially holds the face mask in constant position relative to the mask arm when the face mask is not interfacing with the subject.

12. A mask apparatus according to claim 10, wherein the gasket is formed from a material having a durometer hardness of greater than 45 shore A.

13. A mask apparatus according to claim 10, wherein the gasket is formed from a material having a durometer hardness of approximately 60 shore A.

14. A mask apparatus according to claim 10, wherein the cross-section of the gas outlet of the mask arm is substantially rectangular in shape and the cross-section of the gas inlet of the face mask is substantially triangular in shape.

15. A mask apparatus according to claim 10, wherein the gasket is configured such that the face mask is more easily rotated relative to the mask arm in a first direction than in a second direction perpendicular to the first direction.

16. A mask apparatus according to claim 10, wherein:
the mask arm extends generally in a longitudinal direction; and
the gasket is configured such that the face mask is more easily rotated relative to the mask arm in a lateral direction perpendicular to the longitudinal direction than in the longitudinal direction.

17. A mask apparatus according to claim 10, wherein the gasket includes a reinforced portion that substantially prevents the gasket from collapsing.

18. A mask apparatus according to claim 10, wherein:
the gasket includes a gasket skirt located generally between the face mask and the mask arm assembly, the gasket skirt having a substantially uniform thickness around a first portion of the gasket skirt; and
the reinforced portion of the gasket comprises a second portion of the gasket skirt having a thickness significantly greater than the substantially uniform thickness of the first portion of the gasket skirt.

19. An adjustable gas delivery system, comprising:
a face interfacing means configured to deliver gas to a subject, the face interfacing means including a flexible cushioning means for interfacing with the subject's face and a rigid base means for supporting the cushioning means, the rigid base means including a gas inlet;
a mask support means for delivering gas to the face interfacing means, the mask support means including a gas outlet, the gas outlet of the mask support means having a cross-sectional area smaller than a cross-sectional area of the gas inlet of the base means of the face interfacing means; and
a gasket means coupling the gas outlet of the mask support means with the gas inlet of the face interfacing means, the gasket means being flexible such that the orientation of the face interfacing means relative to the mask support means is adjustable.

20. A system according to claim 19, wherein the cross-section of the gas outlet of the mask support means is substantially rectangular in shape and the cross-section of the gas inlet of the face interfacing means is substantially triangular in shape.

21. A breathing facilitation system for facilitating or affecting a subject's breathing, comprising:
a gas source configured to deliver gas;
an adjustable mask apparatus; and
one or more gas delivery conduits configured to deliver gas from the gas source to a subject via the adjustable mask apparatus;
wherein the adjustable mask apparatus comprises:
a face mask configured to deliver gas to a subject, the face mask including a flexible cushion portion configured to interface with the subject's face and a rigid base portion configured to support the cushion portion, the rigid base portion including a gas inlet;
an arm apparatus configured to deliver gas to the face mask, the arm apparatus including a gas outlet, the gas outlet of the arm apparatus having a cross-sectional area smaller than a cross-sectional area of the gas inlet of the base portion of the face mask; and
a gasket coupling the gas outlet of the arm apparatus with the gas inlet of the face mask, the gasket being flexible such that the orientation of the face mask relative to the arm apparatus is adjustable.

* * * * *